(12) United States Patent
Oliver et al.

(10) Patent No.: US 11,975,112 B2
(45) Date of Patent: May 7, 2024

(54) TREATMENT OF VOMITING AND NAUSEA WITH MINIMUM DOSE OF OLANZAPINE

(71) Applicant: Starton Therapeutics, Inc., Paramus, NJ (US)

(72) Inventors: James Oliver, Raleigh, NC (US); Fotios Plakogiannis, Whitestone, NY (US); Tamanna Lather, Jersey City, NJ (US); Marina Borovinskaya, East Brunswick, NJ (US); Nisarg Modi, Bellerose, NY (US); Rod L. Hartwig, Sloatsburg, NJ (US)

(73) Assignee: Starton Therapeutics, Inc., Paramus, NJ (US)

( * ) Notice: Subject to any disclaimer, the term of this patent is extended or adjusted under 35 U.S.C. 154(b) by 116 days.

(21) Appl. No.: 17/148,262

(22) Filed: Jan. 13, 2021

(65) Prior Publication Data
US 2021/0244679 A1    Aug. 12, 2021

Related U.S. Application Data

(60) Provisional application No. 63/083,759, filed on Sep. 25, 2020, provisional application No. 63/083,774, filed on Sep. 25, 2020, provisional application No. 62/960,611, filed on Jan. 13, 2020, provisional application No. 62/960,582, filed on Jan. 13, 2020.

(51) Int. Cl.
| | |
|---|---|
| *A61K 9/70* | (2006.01) |
| *A61K 9/00* | (2006.01) |
| *A61K 31/5513* | (2006.01) |
| *A61K 47/10* | (2017.01) |
| *A61K 47/12* | (2006.01) |
| *A61K 47/14* | (2017.01) |
| *A61K 47/20* | (2006.01) |
| *A61K 47/38* | (2006.01) |
| *A61P 1/08* | (2006.01) |

(52) U.S. Cl.
CPC .......... *A61K 9/7053* (2013.01); *A61K 9/0053* (2013.01); *A61K 9/7061* (2013.01); *A61K 9/7069* (2013.01); *A61K 31/5513* (2013.01); *A61K 47/10* (2013.01); *A61K 47/12* (2013.01); *A61K 47/14* (2013.01); *A61K 47/20* (2013.01); *A61K 47/38* (2013.01); *A61P 1/08* (2018.01)

(58) Field of Classification Search
CPC .............. A61K 31/5513; A61K 9/0014; A61K 9/0021; A61K 9/7023; A61K 9/703; A61K 9/7038; A61K 9/7046; A61K 9/7053; A61K 9/7061; A61K 9/7069; A61K 9/7076; A61K 9/7084; A61K 9/7092; A61P 1/08
See application file for complete search history.

(56) References Cited

U.S. PATENT DOCUMENTS

2007/0148218 A1*  6/2007  Gordon ................ A61K 9/7061
                                                                514/220

FOREIGN PATENT DOCUMENTS

| CN | 102028695 A | | 4/2011 | |
| GB | 2305860 A | * | 4/1997 | ............. A61K 31/55 |
| WO | WO 2020/131915 A1 | | 6/2020 | |

OTHER PUBLICATIONS

Davis et al., "Nausea and Vomiting: Managing Side Effects from PARP Inhibitors", Oncology (Norwalk), CMP Medica LLC, The Oncology Group, US, vol. 33, No. 2, Feb. 15, 2019, pp. 58-61.
Slimano, et al., "Olanzapine as antiemetic drug in oncology: a retrospective study in non-responders to standard antiemetic therapy", International Journal of Clinical Pharmacy, Springer Netherlands, vol. 40, No. 5, May 9, 2018, pp. 1265-1271.
Yang et al., "Efficacy of olanzapine for the prophylaxis of chemotherapy-induced nausea and vomiting: a meta-analysis", British Journal of Clinical Pharmacology, vol. 83, No. 7, Mar. 23, 2017, pp. 1369-1379.
International Search Report for PCT/US2021/013272, dated Jun. 28, 2021, 16 pages.

* cited by examiner

*Primary Examiner* — Michael B. Pallay
(74) *Attorney, Agent, or Firm* — Dority & Manning, P.A.

(57) ABSTRACT

Compositions, devices, and methods for transdermal administration of olanzapine and uses thereof, e.g., to treat nausea and vomiting.

11 Claims, 10 Drawing Sheets

TREATMENT OF VOMITING AND NAUSEA WITH MINIMUM DOSE OF OLANZAPINE

RELATED APPLICATIONS

The present application claims priority to and the benefit of U.S. Provisional Patent Application No. 62/960,582 and U.S. Provisional Patent Application No. 62/960,611, both filed on Jan. 13, 2020, and U.S. Provisional Patent Application No. 63/083,759 and U.S. Provisional Patent Application No. 63/083,774, both filed on Sep. 25, 2020, the entire contents of each of which are hereby incorporated by reference for all purposes.

TECHNICAL FIELD

The subject matter described herein relates to pharmaceutical compositions comprising olanzapine and oleic acid, and their use, e.g., methods of treatment for vomiting (emesis) and nausea.

BACKGROUND

Olanzapine (2-methyl-10-(4-methyl-1-piperazinyl)-4H-thieno-[2,3-b][1,5]benzo-diazepine), which has a chemical structure shown below, is an antipsychotic medication used to treat schizophrenia and bipolar disorder. It is usually classed with the atypical antipsychotics, a newer generation of antipsychotics. It has been approved by the FDA in tablet form under the brand name ZYPREXA® for treatment of schizophrenia and bipolar mania. Olanzapine has also been investigated for use as an antiemetic at oral doses of 10 mg and 5 mg a day, generally in combination with one or more further agents, e.g. to treat nausea and vomiting after administration of the chemotherapeutic cisplatin.

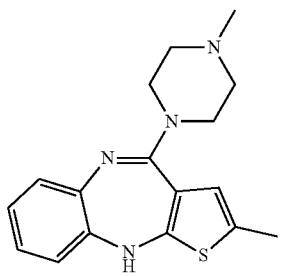 [SMILES: Cc1cc2c(s1)Nc1ccccc1N=C2N1CCN(C)CC1]

Due to side effects, such as fatigue and sedation, associated with the transdermal administration of olanzapine, it is important to identify a minimum effective dose of olanzapine, and find improved compositions, devices, patches, systems, and methods of transdermal delivery of olanzapine and uses thereof, e.g., to treat nausea and vomiting.

BRIEF SUMMARY

The following aspects and embodiments thereof described and illustrated below are meant to be exemplary and illustrative, not limiting in scope.

In one aspect, a method for reducing emesis in a subject in need thereof is provided. The method comprises administering or instructing to administer olanzapine to the subject in an amount greater than about 4 mg and less than about 8 mg.

In another aspect, a method for attenuating frequency of vomiting (emesis) in a subject in need thereof is provided. The method comprises administering or instructing to administer olanzapine to the subject in an amount greater than about 4 mg and less than about 8 mg.

In another aspect, a method for attenuating intensity of vomiting (emesis) in a subject in need thereof is provided. The method comprises administering or instructing to administer olanzapine to the subject in an amount greater than about 4 mg and less than about 8 mg.

In each of the preceding aspects, the amount of olanzapine that is greater than about 4 mg and less than about 8 mg refers to daily amount.

In another aspect, a method of ameliorating nausea in a subject in need thereof is provided. The method comprises administering or instructing to administer olanzapine to the subject in an amount greater than about 2 mg and less than about 6 mg.

In another aspect, a method of reducing frequency of nausea in a subject in need thereof is provided. The method comprises administering or instructing to administer olanzapine to the subject in an amount greater than about 2 mg and less than about 6 mg.

In another aspect, a method of attenuating intensity of nausea in a subject in need thereof is provided. The method comprises administering or instructing to administer olanzapine to the subject in an amount greater than about 2 mg and less than about 6 mg.

In another aspect, a method for reducing frequency of nausea and for attenuating intensity of nausea in a subject in need thereof is provided. The method comprises administering or instructing to administer olanzapine to the subject in an amount greater than about 2 mg and less than about 6 mg.

In another aspect, a method of treating nausea in a subject in need thereof is provided. The method comprises administering or instructing to administer olanzapine to the subject in an amount greater than about 2 mg and less than about 6 mg.

In each of the preceding aspects, the amount of olanzapine that is greater than about 2 mg and less than about 6 mg refers to daily amount.

In another aspect, a method of preventing nausea and/or vomiting associated with chemotherapy in a subject in need thereof is provided. The method comprises administering or instructing to administer olanzapine in an amount greater than about 2 mg and less than about 8 mg, wherein sedation resulting from said administering is essentially unchanged relative to an olanzapine oral dose of about 2 mg.

In another aspect, a method to reduce nausea and/or vomiting associated with chemotherapy in a subject in need thereof is provided. The method comprises administering or instructing to administer olanzapine in an amount greater than about 2 mg and less than about 8 mg, wherein sedation resulting from said administering is essentially unchanged relative to an olanzapine oral dose of about 2 mg.

In each of the preceding aspects, the amount of olanzapine that is greater than about 2 mg and less than about 8 mg refers to daily amount.

In another aspect, a method of treating nausea and/or vomiting induced by a PARP-inhibitor in a subject in need thereof is provided. The method comprises administering a therapeutic effective amount of a PARP-inhibitor to the subject in need thereof, administering or instructing to administer olanzapine to the subject in an daily amount greater than about 2 mg and less than about 8 mg, greater than about 4 mg and less than about 8 mg, or greater than about 2 mg and less than about 6 mg, wherein administering the PARP-inhibitor and olanzapine are performed as part of a common administration scheme. In further embodiments, the common administration scheme is characterized by administering olanzapine about 1 to about 24 hours before administration of the PARP-inhibitor. In other embodiments, the common administration scheme is characterized by co-administering olanzapine and the PARP-inhibitor within a window of time of 1 hour or less.

In another aspect, a composition for transdermal delivery is provided. The composition comprises an adhesive matrix which comprises olanzapine, oleic acid, and one or more of a fatty acid, a fatty alcohol and a fatty ester.

In another aspect, a composition for transdermal delivery is provided. The composition comprises an adhesive, olanzapine, oleic acid, and one or more of a fatty acid, a fatty alcohol and a fatty ester.

In one embodiment, the composition does not comprise another acid (organic or inorganic acid, which is not a polymer or oligomer) which has a pKa lower than that of oleic acid. Such another acid includes acetic acid and trifluoroacetic acid.

In one embodiment, the olanzapine and the oleic acid form an association complex via proton transfer.

In one embodiment, the composition further comprises an emulsifier or a penetration enhancer.

In one embodiment, the emulsifier is a glycerol ester.

In one embodiment, the glycerol ester is selected from the group consisting of glycerol monooleate, glyceryl monotallate, and glyceryl trioleate.

In one embodiment, the penetration enhancer is selected from dimethyl sulfoxide and n-dodecylcaprolactam (Azone).

In one embodiment, the molar amount of olanzapine corresponds to a therapeutically effective amount.

In one embodiment, the therapeutically effective amount is between about 2-50 mg olanzapine.

In one embodiment, the molar amount of olanzapine is selected to deliver between 1-20 such as 1-12 mg olanzapine in 24 hours when the composition is applied to skin.

In one embodiment, the molar ratio of oleic acid to olanzapine is between about 0.5:1 to 5:1 such as 1:1 to 3:1.

In one embodiment, the molar ratio of oleic acid to olanzapine is between about 1:1 to 3:1.

In one embodiment, the molar ratio of oleic acid to olanzapine is between about 1:1 to 2.7:1.

In one embodiment, the molar ratio of oleic acid to olanzapine is between about 1.2:1 to 2.6:1.

In one embodiment, the adhesive matrix comprises a fatty alcohol and a fatty ester.

In one embodiment, the fatty alcohol is myristyl alcohol.

In one embodiment, the fatty ester is isopropyl palmitate.

In one embodiment, the adhesive matrix comprises a polyvinylpyrrolidone.

In one embodiment, the polyvinylpyrrolidone is selected from a cross-linked polyvinylpyrrolidone and a copolymer of polyvinylpyrrolidone.

In one embodiment, the copolymer of polyvinylpyrrolidone is a vinylpyrrolidone-vinyl acetate copolymer.

In one embodiment, the adhesive matrix comprises silicone dioxide.

In one embodiment, the adhesive matrix comprises ethyl cellulose.

In one embodiment, the adhesive matrix further comprises a pressure-sensitive adhesive.

In one embodiment, the pressure-sensitive adhesive is an acrylate copolymer.

In another aspect, a composition for transdermal delivery is provided. The composition comprises (i) at least about 40 wt % of a pressure-sensitive adhesive; (ii) between about 3-15 wt % of a fatty acid ester; (iii) between about 1-20 wt % such as 5-20 wt % olanzapine; and (iv) between about 8-25 wt % oleic acid; and wherein the amount of olanzapine is sufficient to deliver between 1-20 mg such as 1-12 mg olanzapine in 24 hours when the composition is applied to skin.

In one embodiment, the pressure-sensitive adhesive is an acrylate copolymer.

In one embodiment, the fatty acid ester is isopropyl palmitate.

In one embodiment, the molar ratio of oleic acid to olanzapine is between about 1.2:1 to 2.7:1.

In one embodiment, the composition further comprises one or more of a polyvinylpyrrolidone, ethyl cellulose, and silicon dioxide.

In another aspect, a composition for transdermal delivery is provided. The composition consists essentially of (i) at least about 40 wt % of a pressure-sensitive adhesive; (ii) optionally, between about 0.1-25% such as 3-10 wt % of a polyvinylpyrrolidone, ethyl cellulose or silicon dioxide or stabilizing agents; (iii) between about 3-15 wt % of isopropyl palmitate; (iv) between about 6-15 wt % olanzapine; and (v) between about 8-20 wt % oleic acid; and wherein the amount of olanzapine is sufficient to deliver between 1-20 mg such as 1-12 mg olanzapine in 24 hours when the composition is applied to skin.

In another aspect, a transdermal device comprises any of the composition described herein.

In another aspect, a transdermal device for systemic delivery of olanzapine is provided. The transdermal device comprises a drug matrix comprising an acrylate polymer adhesive, a fatty ester, oleic acid, and olanzapine, and wherein the transdermal device when applied to skin delivers (i) an amount of olanzapine effective to alleviate nausea, vomiting, or both within a first period of between about 4-8 hours and (ii) an amount of olanzapine to alleviate nausea, vomiting or both for at least a sustained period of between about 1-7 days.

In one embodiment, the transdermal device when applied to (human cadaver) skin in vitro has an average flux during the sustained period of at least about 4 µg/cm²·hr.

In one embodiment, the sustained period is between about 2-7 days or between 2-5 days.

In one embodiment, the amount of olanzapine delivered in the first period and the sustained period is at least about 3 mg per day.

In one embodiment, the amount of olanzapine delivered in the first period and the sustained period is between about 1-20 such as 3-6 mg per day.

In one embodiment, the drug matrix comprises between about 1-20 wt % such as 5-20 wt % olanzapine.

In another aspect, a transdermal device for delivery of olanzapine is provided. The transdermal device comprises a drug matrix comprising an acrylate polymer adhesive, a fatty ester, oleic acid, and olanzapine, and wherein the transdermal device when applied to skin in vitro has a flux profile where (i) a maximum flux rate is achieved within about 36-54 hours, (ii) between about 65-80% of the maximum flux rate is achieved within about 18-36 hours, and (iii) an average flux rate of at least about 3 µg/cm²·hr for a period of between about 1-7 days is achieved.

In one embodiment, the average flux rate is for a period of between about 1-3 or 1-5 days.

In one embodiment, the flux profile provides over the period an amount of olanzapine effective to alleviate nausea, vomiting, or both.

In one embodiment of the transdermal device, the olanzapine and the oleic acid form an association complex via proton transfer.

In one embodiment of the transdermal device, the drug matrix further comprises an emulsifier or a penetration enhancer.

In one embodiment of the transdermal device, the emulsifier is a glycerol ester.

In one embodiment of the transdermal device, the glycerol ester is selected from the group consisting of glycerol monooleate, glyceryl monotallate, and glyceryl trioleate.

In one embodiment of the transdermal device, the drug matrix further comprises a fatty alcohol such as myristyl alcohol.

In one embodiment of the transdermal device, the penetration enhancer is selected from dimethyl sulfoxide and n-dodecylcaprolactam (Azone).

In one embodiment of the transdermal device, the molar amount of olanzapine corresponds to a therapeutically effective amount.

In one embodiment of the transdermal device, the therapeutically effective amount is between about 2-50 mg olanzapine.

In one embodiment of the transdermal device, the molar amount of olanzapine is selected to deliver between 1-20 such as 1-12 mg olanzapine in 24 hours when the composition is applied to skin.

In one embodiment of the transdermal device, the molar ratio of oleic acid to olanzapine is between about 0.5:1 to 5:1 such as 1:1 to 3:1.

In one embodiment of the transdermal device, the molar ratio of oleic acid to olanzapine is between about 1:1 to 3:1.

In one embodiment of the transdermal device, the molar ratio of oleic acid to olanzapine is between about 1:1 to 2.7:1.

In one embodiment of the transdermal device, the molar ratio of oleic acid to olanzapine is between about 1.2:1 to 2.6:1.

In one embodiment of the transdermal device, the fatty ester is isopropyl palmitate.

In one embodiment of the transdermal device, the drug matrix further comprises a polyvinylpyrrolidone.

In one embodiment of the transdermal device, the polyvinylpyrrolidone is selected from a cross-linked polyvinylpyrrolidone and a copolymer of polyvinylpyrrolidone.

In one embodiment of the transdermal device, the copolymer of polyvinylpyrrolidone is a vinylpyrrolidone-vinyl acetate copolymer.

In one embodiment of the transdermal device, the drug matrix comprises silicone dioxide.

In one embodiment of the transdermal device, the drug matrix comprises ethyl cellulose.

In one embodiment of the transdermal device, the drug matrix comprises butylated hydroxy toluene (BHT).

In another aspect, a method of treating nausea and/or vomiting in a subject in need thereof is provided. The method comprises transdermally administering olanzapine to the subject in a dose ranging from 2.0 mg to 6.0 mg daily. The dose can be ascertained as "apparent daily dose", which as used in this application refers to the difference between the drug load on the transdermal device before the administration and the residual drug on the transdermal device obtained after the administration divided by the days of the transdermal device applied to the subject.

In another aspect, a method of treating nausea and/or vomiting in a subject in need thereof is provided. The method comprises transdermally administering olanzapine to the subject, wherein the method achieves an AUC of olanzapine ranging from 1000 to 2500 µg/L/h.

In another aspect, a method of treating nausea and/or vomiting in a subject in need thereof is provided. The method comprises transdermally administering olanzapine to the subject, wherein the method achieves a mean Cmax ranging from 5 to 20 µg/L.

In another aspect, a method of treating nausea and/or vomiting in a subject in need thereof is provided. The method comprises transdermally administering olanzapine to the subject, wherein the method achieves an AUC of olanzapine of between 20% and 80% of the AUC obtained from a standard of care treatment.

In each of the preceding aspect, the olanzapine is administered in the form of a composition or transdermal device as disclosed herein.

In some embodiments of each of the preceding aspect, the nausea and/or vomiting is induced by chemotherapy or a PARP inhibitor, wherein the chemotherapy or PARP inhibitor can be administered before, after, or at the same time as olanzapine is administered.

DETAILED DESCRIPTION

I. Definitions

Figure 1:
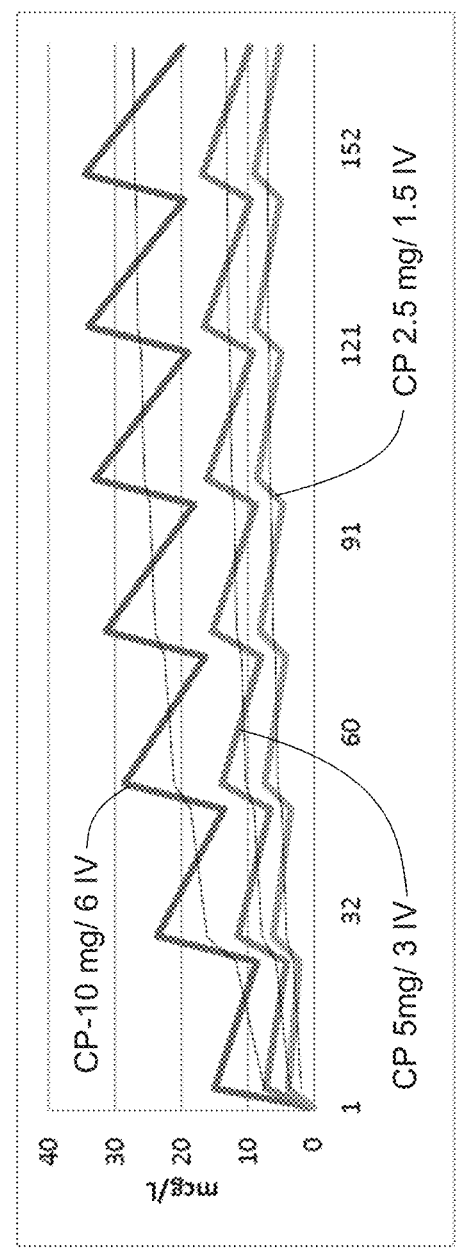
FIG. 1 shows an in silico modeling of plasma level of olanzapine over a 7-day dosing interval which achieves steady state at oral doses of 10 mg, 5 mg, and 2.5 mg a day and the planned patch plasma level targets to emulate each specific oral dose.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Compositions, devices, and methods described herein are not limited to the specific polymers, excipients, cross-linking agents, additives, manufacturing processes, or adhesive products described herein. It will be understood that the particular terminology used herein is for the purpose of describing particular embodiments and is not intended to be limiting.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to a "solvent" includes a single solvent as well as two or more of the same or different solvents, and the like.

The term fatty alcohol refers to a compound with the formula ROH, wherein R is $C_{2-30}$ alkyl or $C_{3-30}$ alkenyl comprising one, two, three, or four double bonds.

The term fatty ester refers to an ester result from the combination of fatty acid with an alcohol, wherein the fatty acid and alcohol is a compound with the formula RCOOH and $R(OH)_{1-3}$, respectively, wherein R is $C_{1-30}$ alkyl (hydrocarbon) or $C_{3-30}$ alkenyl comprising one, two, three, or four double bonds. Exemplary fatty acids include, without limitation, capric acid, lauric acid, palmitic acid, stearic acid, elaidic acid (C18:1), gondoic acid (C20:1), erucic acid (C22:1), nervonic acid (C24:1), and ximenic acid (C26:1), hexadecatrienoic acid (16:3), linoleic acid (C18:2), alpha-linolenic acid (C18:3), gamma-linolenic acid (C18:3), calendic acid (C18:3), stearidonic acid (C18:4) mead acid (C20:3), eicosadienoic acid (C20:3), eicosatrienoic acid (C20:3), dihomo-gamma-linolenic acid (C20:3), arachidonic acid (C20:4), and docosadienoic acid (C22:2).

The term "active agent" as used herein refers to a chemical material or compound suitable for topical or transdermal administration and that induces a desired effect. The terms include agents that are therapeutically effective, prophylactically effective, and cosmetically effective agents. The terms "active agent," "drug," and "therapeutic agent" are used interchangeably herein.

An "adhesive matrix" as described herein includes matrices made in one piece, for example, matrices made via solvent casting or extrusion as well as matrices formed in two or more portions that are then pressed or joined together.

"PARP" as used herein refers to a group of poly (ADP-ribose) polymerase enzymes (PARP). PARP enzymes are activated by DNA damage, in particular, PARP1 and PARP2 enzymes. These enzymes facilitate DNA repair in pathways involving single-strand breaks (SSBs) and base excision repair (BER). All PARP-inhibitors are generally believed to inhibit both PARP1 and PARP2. The suppression of PARP catalytic activity prevents the formation of poly (ADP-ribose) polymers and blocks the binding of NAD+ at the site of DNA damage, ultimately compromising a cell's ability to overcome DNA-dependent damage.

"PARP-inhibitor" as used herein refers to a chemical compound that blocks an enzyme in cells called poly (ADP-ribose) polymerase (PARP). PARP enzymes help repair DNA upon damage. DNA damage may be caused by various things, including exposure to UV light, radiation, certain anticancer drugs, or other substances in the environment. Many PARP-inhibitors share certain structural commonalities, and typically include a benzamide moiety, or a benzamide-derivative moiety, and find use as chemotherapeutic agents directed at targeting cancers with defective DNA-damage repair. Blocking PARP keeps cancer cells from repairing their damaged DNA, thus causing them to die.

Examples of PARP inhibitors include olaparib (AZD-2281, Lynparza® by Astra Zeneca), e.g. for breast, ovarian, colorectal or prostate cancer, rucaparib (PF-01367338, Rubraca® by Clovis Oncology), e.g. for metastatic breast and ovarian cancer, niraparib (MK-4827, Zejula® by Tesaro), e.g. for epithelial ovarian, fallopian tube, and primary peritoneal cancer, talazoparib (BMN-673, originally developed by BioMarin Pharmaceutical Inc., currently in development by Pfizer), e.g. for advanced hematological malignancies and for advanced or recurrent solid tumors and for metastatic germline BRCA mutated breast cancer, veliparib (ABT-888, developed by AbbVie), e.g. for advanced ovarian cancer, triple-negative breast cancer, non-small cell lung cancer (NSCLC), and metastatic melanoma, CEP 9722 for non-small-cell lung cancer (NSCLC), E7016 (developed by Eisai), e.g. for melanoma, BGB-290, iniparib, 3-aminobenzamide (3-AB, a prototypical PARP inhibitor), PJ-34, Nu1085, INO-1001, CEP-8933/CEP-9722, and nicotinamide.

The term "skin" as used herein refers to skin or mucosal tissue, including the interior surface of body cavities that have a mucosal lining. The term "skin" should be interpreted as including "mucosal tissue" and vice versa.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

The terms "transdermal" or "transdermal delivery" as used herein refer to administration of an active agent to a body surface of an individual so that the agent passes through the body surface (e.g., through the skin) and into the individual's blood stream. The term "transdermal" is intended to include transmucosal administration, i.e., administration of a drug to the mucosal (e.g., sublingual, buccal, vaginal, rectal, etc.) surface of an individual so that the agent passes through the mucosal tissue and into the individual's blood stream.

II. Methods of Treatment

Olanzapine is an antipsychotic medication used to treat schizophrenia and bipolar disorder. It is usually classed with the atypical antipsychotics, a newer generation of antipsychotics. Olanzapine has also been investigated for use as an antiemetic at oral doses of 10 mg and 5 mg a day, generally in combination with one or more further agents, e.g. to treat nausea and vomiting after administration of the chemotherapeutic cisplatin.

Methods of treating vomiting (emesis) and/or nausea by administration of or instruction to administering olanzapine are described herein.

A. Olanzapine in an Amount Greater than about 4 mg and Less than about 8 mg

In one aspect, a method for reducing emesis in a subject in need thereof is provided. The method comprises administering or instructing to administer olanzapine to the subject in an amount greater than about 4 mg and less than about 8 mg.

In another aspect, a method for attenuating frequency of vomiting (emesis) in a subject in need thereof is provided. The method comprises administering or instructing to administer olanzapine to the subject in an amount greater than about 4 mg and less than about 8 mg.

In another aspect, a method for attenuating intensity of vomiting (emesis) in a subject in need thereof is provided. The method comprises administering or instructing to administer olanzapine to the subject in an amount greater than about 4 mg and less than about 8 mg.

In each of the preceding aspects, the administering or instructing to administer can be oral or transdermally administering.

In some embodiments, the transdermally administration provides a plasma concentration of olanzapine i) 24 hours after administration of at least about 7 μg/L, ii) 48 hours after administration of greater than about 11 μg/L, and iii) 60 hours after administration of greater than about 15 μg/L.

In some embodiments, the transdermal administration provides a plasma concentration of olanzapine 24 hours after administration of at least about 6 μg/L and achieves a steady state plasma concentration of olanzapine of about 16-24 μg/L for a period beginning at a time 24 hours after administration and continuing for at least about 2 days.

In some embodiments, the transdermal administration provides a plasma concentration of olanzapine 24 hours after administration of at least about 8 μg/L and achieves a steady state plasma concentration of olanzapine of about 18-22 μg/L for a period beginning at a time 24 hours after administration and continuing for at least about 2 days.

In some embodiments, the period of steady state plasma concentration achieved in the transdermal administration continues for at least about 3 days, 4 days, 5 days or 6 days.

In each of the preceding aspects and embodiments, the emesis can be associated with chemotherapy.

In each of the preceding aspects and embodiments, sedation resulting from the administration can be essentially unchanged relative to an olanzapine oral dose of about 2 mg.

B. Olanzapine in an Amount Greater than about 2 mg and Less than about 6 mg

In one aspect, a method of ameliorating nausea in a subject in need thereof is provided. The method comprises administering or instructing to administer olanzapine in an amount greater than about 2 mg and less than about 6 mg. In some embodiments, nausea is ameliorated by reducing frequency of nausea and/or attenuating intensity of nausea.

In another aspect, a method of reducing frequency of nausea in a subject in need thereof is provided. The method comprises administering or instructing to administer olanzapine to the subject in an amount greater than about 2 mg and less than about 6 mg.

In another aspect, a method of attenuating intensity of nausea in a subject in need thereof is provided. The method comprises administering or instructing to administer olanzapine to the subject in an amount greater than about 2 mg and less than about 6 mg.

In another aspect, a method for reducing frequency of nausea and for attenuating intensity of nausea in a subject in need thereof is provided. The method comprises administering or instructing to administer olanzapine to the subject in an amount greater than about 2 mg and less than about 6 mg.

In another aspect, a method of treating nausea in a subject in need thereof is provided. The method comprises administering or instructing to administer olanzapine to the subject in an amount greater than about 2 mg and less than about 6 mg.

In each of the preceding aspects or embodiments, the administering or instructing to administer can be oral or transdermally administering.

In some embodiments, the transdermal administration provides a plasma concentration of olanzapine 24 hours after administration of at least about 3 μg/L and achieves a steady state plasma concentration of olanzapine of about 10-16 μg/L for a period beginning at a time 24 hours after administration and continuing for at least about 2 days.

In some embodiments, the transdermal administration provides a plasma concentration of olanzapine 24 hours after administration of at least about 4 μg/L and achieves a steady state plasma concentration of olanzapine of at least about 11 μg/L for a period beginning at a time 24 hours after administration and continuing for at least about 2 days.

In some embodiments, the transdermal administration provides a plasma concentration of olanzapine 24 hours after administration of at least about 5 μg/L and achieves a steady state plasma concentration of olanzapine of at least about 13 μg/L for a period beginning at a time 24 hours after administration and continuing for at least about 2 days.

In some embodiments, the period of steady state plasma concentration achieved in transdermal administration continues for at least about 3 days, 4 days, 5 days or 6 days.

In each of the preceding aspects or embodiments, the nausea can be chronic nausea or acute nausea.

In each of the preceding aspects or embodiments, the nausea can be associated with chemotherapy.

In each of the preceding aspects or embodiments, sedation resulting from the administering can be essentially unchanged relative to an olanzapine dose of about 2 mg.

C. Olanzapine in an Amount Greater than about 2 mg and Less than about 8 mg

In one aspect, a method of preventing nausea and vomiting associated with chemotherapy in a subject in need thereof is provided. The method comprises administering or instructing to administer olanzapine in an amount greater than about 2 mg and less than about 8 mg, wherein sedation resulting from said administering is essentially unchanged relative to an olanzapine oral dose of about 2 mg.

In another aspect, a method to reduce nausea and vomiting associated with chemotherapy in a subject in need thereof is provided. The method comprises administering or instructing to administer olanzapine in an amount greater than about 2 mg and less than about 8 mg, wherein sedation resulting from said administering is essentially unchanged relative to an olanzapine oral dose of about 2 mg.

In each of the preceding aspect, the administering or instructing to administer can be oral or transdermal administering.

In each of the preceding aspects and embodiments, the method can reduce intensity of nausea, frequency of vomiting, or both.

In each of the preceding aspects and embodiments, the administering can prevent and/or reduce nausea and vomiting in an acute phase that is during and/or for the first 24 hours after chemotherapy.

In each of the preceding aspects and embodiments, the method can reduce intensity of nausea, frequency of vomiting or both in a delayed phase that is 24-120 hours after chemotherapy.

In each of the preceding aspects and embodiments, the chemotherapy can be highly emetogenic cancer chemotherapy.

In each of the preceding aspects and embodiments, the chemotherapy can be initial and repeat administration of moderately emetogenic cancer chemotherapy.

D. Transdermal Methods of Treatment

In one aspect, the method comprises transdermally administering or instructing to transdermally administer olanzapine to the subject in a dose ranging from 2.0 mg to 6.0 mg daily. The transdermal dose can be ascertained as "apparent daily dose", which as used in this application refers to the difference between the drug load on the transdermal device before the administration and the residual drug on the transdermal device obtained after the administration divided by the days of the transdermal device applied to the subject. In some embodiments, the apparent dose can be from 3.0 to 5.1 mg, 3.1 to 5.0 mg, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0 mg daily.

In another aspect, the method comprises transdermally administering or instructing to transdermally administer olanzapine to the subject, wherein the method achieves an AUC of olanzapine ranging from 1000 to 2500 µg/L/h. In some embodiments, the AUC of olanzapine is from 1200 to 2200 µg/L/h, 1400 to 2200 µg/L/h, 1200, 1250, 1300, 1350, 1400, 1450, 1500, 1550, 1600, 1650, 1700, 1750, 1800, 1850, 1900, 1950, 2000, 2050, 2100, 2150, or 2200 µg/L/h.

In another aspect, the method comprises transdermally administering or instructing to transdermally administer olanzapine to the subject, wherein the method achieves a mean Cmax ranging from 5 to 20 µg/L. In some embodiments, the mean Cmax ranges from 5 to 15 µg/L, 8 to 15 µg/L, 5, 6, 7, 8, 9, 10, 11, 12, 13, 14, 15, or 16 µg/L.

In another aspect, the method comprises transdermally administering or instructing to transdermally administering olanzapine to the subject, wherein the method achieves an AUC of olanzapine of between 20% and 80% of the AUC obtained from a standard of care treatment. In some embodiments, the AUC ranges from 25% to 70%, 25% to 60%, or 25% to 50%.

In some embodiments of each of the preceding aspects, the subject is less hungry and sedated than a subject undergoing a standard of care of treatment. As used herein, the standard of care treatment comprises daily oral dose of 5 or 10 mg of olanzapine.

In some embodiments of each of the preceding aspect, the nausea and/or vomiting is induced by chemotherapy or a PARP inhibitor, wherein the chemotherapy or PARP inhibitor can be administered before, after, or at the same time as olanzapine is administered.

In some embodiments, olanzapine is administered about 1 to about 24 hours before administration of the PARP-inhibitor. In some embodiments, olanzapine and the PARP-inhibitor are administered within a window of time of 1 hour or less.

In each of the preceding aspects of the method, the olanzapine is administered in the form of a composition or transdermal device as disclosed herein.

Example 5 describes a comparative bioavailability (BA) study in healthy female volunteers to characterize the olanzapine systemic exposure profile of a transdermal device as described herein of two different sizes applied for 7-days compared to that of a once daily 7-day regimen of olanzapine 10 mg/day. The systemic exposure modeled in silico demonstrated by AUC0-∞, of the transdermal device used in the study herein was dosed to be less than a 10 mg dose of oral olanzapine. See FIG. 8.

Example 5 also describes the hunger score and sedation scores for each treatment group. The cumulative sum total of intensity scores of diary response scored twice-daily to a question of hunger on an ordinal scale of 0-10 (maximum cumulative sum total of intensity score was 250 and minimum is 0). The cumulative sum total of intensity scores for hunger were significantly lower with transdermal delivery than oral dosing (P<0.008) while there was no difference in the hunger scores between Cohort 2 and 3 (P=0.19). These results do not appear to be dose related as the hunger scores with arithmetically higher in the lower dose patch Cohort. See FIG. 9. The cumulative sum total of intensity scores of diary response score to a twice-daily question of tired/sedation on an ordinal scale of 0-10 (maximum cumulative sum total of intensity score was 250 and minimum is 0). The cumulative sum total of intensity for sedation were arithmetically lower with transdermal delivery than oral dosing (P=0.09). See FIG. 10.

III. Compositions Comprising Olanzapine

In the methods described herein, olanzapine can be administered in the form of a formulation suitable for oral or transdermal administration.

A. Compositions for Oral Administration of Olanzapine

The oral formulation comprises olanzapine and a pharmaceutically acceptable carrier. The oral formulation can be a tablet comprising 2 mg, 4 mg, 6 mg, or 8 mg of olanzapine. The tablet can further comprise a pharmaceutically acceptable carrier including carnauba wax, crospovidone, hydroxypropyl cellulose, hypromellose, lactose, magnesium stearate, and microcrystalline cellulose.

In the methods described herein, olanzapine can also be administered in the form of a composition suitable for transdermal delivery. The transdermal composition comprises an adhesive matrix comprising olanzapine, oleic acid, and one or more of a fatty acid, a fatty alcohol and a fatty ester.

In some embodiments, the transdermal composition does not comprise another acid (organic or inorganic acid, which is not a polymer or oligomer) which has a pKa lower than that of oleic acid. Such another acid includes acetic acid and trifluoroacetic acid.

In some embodiments, the olanzapine and the oleic acid form an association complex via proton transfer.

In some embodiments, the composition further comprises an emulsifier or a penetration enhancer.

In some embodiments, the emulsifier is a glycerol ester. In some embodiments, the glycerol ester is selected from the group consisting of glycerol monooleate, glyceryl monotallate, and glyceryl trioleate.

In some embodiments, the penetration enhancer is selected from dimethyl sulfoxide and n-dodecylcaprolactam (Azone).

In some embodiments, the molar amount of olanzapine corresponds to a therapeutically effective amount. In some embodiments, the therapeutically effective amount is between about 2-50 mg olanzapine.

In some embodiments, the molar amount of olanzapine is selected to deliver between 1-20 mg such as 1-12 mg olanzapine in 24 hours when the composition is applied to skin.

In some embodiments, the molar ratio of oleic acid to olanzapine is between about 0.5:1 to 5:1 such as 1:1 to 3:1. In some embodiments, the molar ratio of oleic acid to olanzapine is between about 1:1 to 2.7:1. In some embodiments, the molar ratio of oleic acid to olanzapine is between about 1.2:1 to 2.6:1.

In some embodiments, the adhesive matrix comprises a fatty alcohol and a fatty ester.

In some embodiments, the fatty alcohol is myristyl alcohol. In some embodiments, the fatty ester is isopropyl palmitate.

In some embodiments, the adhesive matrix comprises a polyvinylpyrrolidone.

In some embodiments, the polyvinylpyrrolidone is selected from a cross-linked polyvinylpyrrolidone and a copolymer of polyvinylpyrrolidone. In some embodiments, the copolymer of polyvinylpyrrolidone is a vinylpyrrolidone-vinyl acetate copolymer.

In some embodiments, the adhesive matrix comprises silicone dioxide. In some embodiments, the adhesive matrix comprises ethyl cellulose. In some embodiments the adhesive matrix further comprises a pressure-sensitive adhesive. In some embodiments, the pressure-sensitive adhesive is an acrylate copolymer.

In the methods described herein, olanzapine can also be transdermally administered in the form of a composition comprising: (i) at least about 40 wt % of a pressure-sensitive adhesive; (ii) between about 3-15 wt % of a fatty acid ester; (iii) between about 1-20 wt % such as 5-20 wt % olanzapine; and (iv) between about 8-25 wt % oleic acid; and wherein the amount of olanzapine is sufficient to deliver between 1-20 mg such as 1-12 mg olanzapine in 24 hours when the composition is applied to skin. In some embodiments, olanzapine can be administered in the form of a transdermal patch comprising the above composition.

In some embodiments, the pressure-sensitive adhesive is an acrylate copolymer.

In some embodiments, the fatty acid ester is isopropyl palmitate.

In some embodiments, the molar ratio of oleic acid to olanzapine is between about 1.2:1 to 2.7:1.

In some embodiments, the composition further comprises one or more of a polyvinylpyrrolidone, ethyl cellulose, and silicone dioxide.

In the methods described herein, olanzapine can also be transdermally administered in the form of a composition consisting essentially of (i) at least about 40 wt % of a pressure-sensitive adhesive; (ii) optionally, between about 0.1-25 wt % such as 3-10 wt % of a polyvinylpyrrolidone, ethyl cellulose or silicon dioxide; (iii) between about 3-15 wt % of isopropyl palmitate; (iv) between about 6-15 wt % olanzapine; and (v) between about 8-20 wt % oleic acid; and wherein the amount of olanzapine is sufficient to deliver between 1-20 mg such as 1-12 mg olanzapine in 24 hours when the composition is applied to skin. In other words, olanzapine can be administered in the form of a transdermal patch. In some embodiments, olanzapine can be administered in the form of a transdermal patch comprising the above composition.

In the methods described herein, olanzapine can also be transdermally administered in the form of a composition consisting essentially of (i) about 56 wt % of a pressure-sensitive adhesive; (ii) about 10 wt % ethyl cellulose; (iii) about 10 wt % isopropyl palmitate; (iv) about 8 wt % olanzapine; (v) about 16 wt % of oleic acid; and (vi) about 0.5 wt % of butylated hydroxytoluene. In some embodiments, olanzapine can be administered in the form of a transdermal patch comprising the above composition.

In some embodiments, the amount of olanzapine in the transdermal patch or formulation is sufficient to deliver olanzapine with an AUC thereof that is between 1% and 80%, 10% and 80%, 20% and 80%, 30% and 80%, or 40% and 80% of the exposure obtained from a standard of care treatment. The standard of care treatment can be 2.5 mg, 4 mg, 5 mg, 6 mg, 8 mg, 10 mg, 15 mg, 20 mg, or 25 mg of olanzapine compound once daily or once every two days via oral administration.

In some embodiments, the amount of olanzapine in the transdermal patch or formulation is sufficient to provide a plasma level of olanzapine that emulates an oral dose, wherein the oral dose can be 4 mg, 5 mg, 6 mg, 8 mg, or 10 mg per day. The term "emulates" can be understood from disclosure herein related to FIG. 1 and Example 1.

A patch may be formed, for example, without limitation, by solvent casting the composition onto a backing layer or release liner, and sandwiching between both, as described herein. Many suitable materials for the backing layer and release liner are known, and include polymer films, fabrics and non-woven materials, e.g. continuous films that prevent ingress of external moisture into the adhesive layer from activities such as showering or bathing. The backing and release liner should preferably be occlusive, or substantially occlusive. Such films include, without limitation, polypropylene, polyvinyl chloride, cellulose acetate, ethyl cellulose, polyurethane, polyethylene, and polyester. Optionally, the backing may be a layered composite that include a metal, such as, without limitation aluminum, e.g. polyethylene terephthalate-aluminium-polyethylene composites, or e.g. a polyester and an ethylene vinyl acetate copolymer heat seal layer (particularly as a backing), or e.g. a fluoropolymer coated polyester film (particularly as a release liner. Suitable backing layers include, without limitation, Scotchpak 1006, 1022, 1109, 9723, 9732, 9733 (3M company); suitable release liners include, without limitation, Scotchpak 1006, 9709, 9741, 9742, 9744, and 9755 (3M company). The thickness of the backing layer and of the release liner is generally more than 10 μm and less than 200 typically about 20 μm to about 120 e.g. about 40 μm to about 100 μm.

The coating formulation for the patch, may comprise volatile solvents which are removed from the patch matrix upon its drying; such volatile solvents include: methanol, ethanol, propanol, 1-propanol, 2-propanol, ethyl acetate, acetone, dichloromethane, chloroform, toluene, and IPA.

Transdermal compositions, devices, and/or systems described herein may be designed for long term use and/or continuous administration of olazapine. It will be appreciated that the total dose of olanzapine per transdermal device will be determined by the size of the device, and/or the loading of olanzapine within the adhesive matrix. In some embodiments, the application period for the transdermal device is between about 1-10 days, 1-7 days, 1-5 days, 1-2 days, 1-3 days, 1-4 days, 3-10 days, 3-7 days, 3-5 days. 5-10 days, and 5-7 days, inclusive. In some embodiments, olanzapine is released from the adhesive matrix as a continuous and/or sustained release over the application period.

Usage of the described transdermal and topical systems described here will have dosages that vary depending on the mode of administration, the particular condition to be treated and the effect desired. Dosage may be transdermal application once daily for 1 day, 2 days, 3, day, 4 days, 5, days, 6 days, 7 days, 8 days, 9 days, 10 days, 11 days, 12 days, 13 days, or 14 days, or longer. Alternatively, application may be several times a day for 1 day, 2 days, 3, day, 4 days, 5, days, 6 days, 7 days, 8 days, 9 days, 10 days, 11 days, 12 days, 13 days, or 14 days, or longer. Alternatively transdermal application may be once every day, every 2 days, every 3 days every 4 days, every 5 days, every 6 days, every 7 days, every 8 days, every 9 days, every 10 days, every 11 days, every 12 days, every 13 days, or every 14 days.

In some embodiments, the transdermal or topical formulations provide for a predetermined rate of delivery of the active components of the transdermal patch over a predetermined time period. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is a constant rate.

In yet further embodiments, the transdermal or topical formulations described herein provide a steady absorption rate of the active components of the transdermal patches by the patient over a predetermined time. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is a constant rate.

In yet further embodiments, the transdermal or topical formulations described herein provide a range of predetermined blood serum levels of the active components of the transdermal patches in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations described herein provide a plasma concentration of the active components of the transdermal patches in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations described herein allow for reduced variability in dosage of the active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In some embodiments, the transdermal or topical formulation provided herein may be administered in dosage regimens such as once in a day, once in two days, once in three days, once in four days, once in five days, once in six days, once in a week, once in 8 to about 13 days, once in two weeks, once in 15 days to about 30 days.

In yet further embodiments, a pharmacokinetic assessment is performed on a blood sample of a subject who has been treated using the transdermal delivery systems described herein. The transdermal formulations described herein are adjusted in response to the pharmacokinetic assessment. For example, the dosage may be adjusted such that a smaller patch, larger patch, or multiple transdermal patches are applied to the subject, or a patch having a more or less of a dose of active ingredients may be applied. In some embodiments, the formulation will be available in various dosage strengths and patch sizes in order to achieve optimum therapeutic outcome based on the subject's requirements.

Examples 2-5 discloses transdermal compositions can be used in the methods disclosed herein.

Example 2 describes preparation of olanzapine transdermal patches labeled as OLA 1, OLA 2, OLA 3, OLA 4, OLA 5, OLA 6, and OLA 7.

In the permeation study as described in Example 3, using OLA 1 as an example, the flux increased rapidly reaching 72% of maximum within the first 24 hours and maximum at about 48 hours. After this, the transdermal flux gradually decreased at a steady rate to about 61% of maximum at 168 hours. The average flux from 24 to 168 hours for 11 donors (50 total replicates) was 4±1.3 ug/hr/sqcm. See FIG. 7.

Example 4 compares the cold flow property of two compositions. The results indicated that composition with an additional polymer such as ethyl cellulose has reduced cold flow.

Example 5 describes a comparative bioavailability (BA) study in healthy female volunteers to characterize the olanzapine systemic exposure profile of a transdermal device as described herein of two different sizes applied for 7-days compared to that of a once daily 7-day regimen of olanzapine 10 mg/day. The systemic exposure modeled in silico demonstrated by AUCO-∞, of the transdermal device used in the study herein was dosed to be less than a 10 mg dose of oral olanzapine. See FIG. 8.

Example 5 also describes the hunger score and sedation scores for each treatment group. The cumulative sum total of intensity scores of diary response scored twice-daily to a question of hunger on an ordinal scale of 0-10 (maximum cumulative sum total of intensity score was 250 and minimum is 0). The cumulative sum total of intensity scores for hunger were significantly lower with transdermal delivery than oral dosing (P<0.008) while there was no difference in the hunger scores between Cohort 2 and 3 (P=0.19). These results do not appear to be dose related as the hunger scores with arithmetically higher in the lower dose patch Cohort. See FIG. 9. The cumulative sum total of intensity scores of diary response score to a twice-daily question of tired/sedation on an ordinal scale of 0-10 (maximum cumulative sum total of intensity score was 250 and minimum is 0). The cumulative sum total of intensity scores for sedation were arithmetically lower with transdermal delivery than oral dosing (P=0.09). See FIG. 10.

B. Compositions for Transdermal Delivery of Olanzapine

In some aspects, provided are compositions comprising an adhesive matrix comprising olanzapine, oleic acid, and one or more of a fatty acid, a fatty alcohol and a fatty ester.

In some embodiments, the adhesive matrix comprises a pressure sensitive adhesive.

The pressure sensitive adhesive includes, without limitation, one or more of: Duro-Tak® 87-2196, Duro-Tak® 387-2051, Duro-Tak® 87-2194, Duro-Tak® 87-235A, Duro-Tak® 387-2054, Duro-Tak® 87-900A, Duro-Tak® 87-9301, Duro-Tak® 387-2516, Duro-Tak® 387-2510, Duro-Tak® 280-2516, Duro-Tak® 87-4098, GELVA GMS® 788, GELVA GMS® 9073, Duro-Tak® 387-2353, Duro-Tak® 87-2074, Duro-Tak® 387-2287, Duro-Tak® 87-2852, Duro-Tak® 87-2054, GELVA® 737, Duro-Tak® 80-1196, Duro-Tak® 87-2070, Duro-Tak® 87-2979, Duro-Tak® 87-2888, and Duro-Tak® 87-2296. Exemplary silicone PSA include, without limitation, one or more of: BIO-PSA® 7-4401, BIO-PSA® 7-4402, BIO-PSA® 7-4501, BIO-PSA® 7-4502, BIO-PSA® 7-4601, BIO-PSA® 7-4602, (Dow Corning®, Dow Chemicals, Midland Mich.), SRS7-4502, SRS7-4501, SRS7-4602, SRS7-4602, amine compatible silicone PSA, a rubber PSA. Exemplary amine compatible silicone PSA include, without limitation, one or more of BIO-PSA® 7-4101, BIO-PSA® 7-4102, BIO-PSA® 7-4201, BIO-PSA® 7-4202, BIO-PSA® 7-4301, BIO- PSA® 7-4302. Exemplary rubber PSA include, without limitation, one or more of: polyisobutylene of low molecular weight, polyisobutylene of medium molecular weight, polyisobutylene of high molecular weight (including, e.g., polyisobutylene 1100000 MW, 35000 MW, 800000 MW, 55000 MW, 2300 MW, or mixtures thereof), Duro-Tak® 87-6908, and polyisobutylene/polybutene adhesive.

Adhesives that may be particularly suitable for the drug-in-adhesive patches and formulations therefore described herein include, without limitation, an acrylate copolymer, such as high molecular weight or highly crosslinked adhesives, typically available as self crosslinkable acrylic adhesives. Examples of such adhesives include, without limitation, Duro-Tak® 387-2516, Duro-Tak® 387-2051, Duro-Tak® 87-2852, Duro-Tak® 87-2194 and Duro-Tak® 87-2852 self crosslinkable acrylic adhesives (available from National Starch and Chemical Company, 10 Finderne Ave., P.O. Box 6500, Bridgewater, N.J. 08807-0500), and GELVA® 737, GELVA® 2655, and GELVA® 1753 self crosslinkable acrylic adhesives (Monsanto's Chemical Group, 730 Worcester Street, Springfield, Mass. 01151).

Duro-Tak® 387-2516 is an acrylic copolymer adhesive containing EHA, vinyl acetate and hydroxyethyl acrylate and is commercially available from National Starch and Chemical Co, Bridgewater, N.J.). Alternatively, the adhesive may be an acrylic adhesive having one or more of hydroxyl functional groups and carboxyl functional groups. Still alternatively, the acrylic adhesive may be a "nonfunctional" adhesive which does not contain function groups (e.g. lacks —OH groups, —COOH groups, or both). Preferably the acrylic adhesive may be a pressure sensitive adhesive (PSA).

In some embodiments, the adhesive matrix comprises a fatty ester. In some embodiments, the adhesive matrix comprise a fatty alcohol and fatty ester.

Fatty alcohol may include, without limitation, one or more saturated, monounsaturated or polyunsaturated fatty alcohol; which may include, without limitation, one or more of: butanol (C4), butyl alcohol (C4), tert-butyl alcohol (C4), tert-amyl alcohol (C5), 3-Methyl-3-pentanol (C6), capryl alcohol (C8), pelargonic alcohol (C9), capric alcohol (C10), Undecyl alcohol (C11), Lauryl alcohol (C12), Tridecyl alcohol (C13), Myristyl alcohol (C14), Pentadecyl alcohol (C15), Cetyl alcohol (C16), Palmitoleyl alcohol (cis-9-hexadecen-1-ol, C16H32O), Heptadecyl alcohol (1-n-heptadecanol, C17H36O), Stearyl alcohol (C18:0), Oleyl alcohol (C18H36O, C18:1), linoleyl alcohol (C18H34O, cis,cis-9,12-Octadecadien-1-ol), Nonadecyl alcohol (C19), Arachidyl alcohol (C20H42O), octyldodecanol (C20H42O, 2-Octyldodecan-1-ol), Heneicosyl alcohol (C21), Behenyl alcohol (C22H46O), Erucyl alcohol (cis-13-docosen-1-ol, C22H44O), Lignoceryl alcohol (C24), and Ceryl alcohol (C26). Saturated fatty alcohol permeation enhancers may include, without limitation, one or more of: lauryl alcohol (C12), isolauryl alcohol (C12, 10-methyl-1-hendecanol), anteisolauryl alcohol (C12, 9-methyl-1-hendecanol), myristyl alcohol (C14), isomyristyl alcohol (C14, 12-methyl-1-tridecanol), anteisomyristyl alcohol (C14, 11-methyl-1-tridecanol), cetyl alcohol (C16), isopalmityl alcohol (C16, 14-methyl-1-pentadecanol), anteisopalmityl alcohol (C16, 13-methyl-1-pentadecanol), stearyl alcohol (C18), isostearyl alcohol (C18, 16-methyl-1-heptadecanol), and anteisostearyl alcohol (C18, 15-methyl-1-pentadecanol). In some embodiments, the fatty alcohol is myristyl alcohol.

Fatty ester is the product formed by reacting an alcohol with a fatty acid. Exemplary fatty ester includes isopropyl palmitate, isopropyl myristate, 2-ethylhexyl palmitate, glyceryl oleate (mono-, di-, or tri-oleate) and 2-ethylhexyl stearate. In some embodiments, the fatty ester is isopropyl palmitate.

Fatty acids that can be included in the composition include, without limitation, capric acid, lauric acid, palmitic acid, stearic acid, elaidic acid (C18:1), gondoic acid (C20:1), erucic acid (C22:1), nervonic acid (C24:1), and ximenic acid (C26:1), hexadecatrienoic acid (16:3), linoleic acid (C18:2), alpha-linolenic acid (C18:3), gamma-linolenic acid (C18:3), calendic acid (C18:3), stearidonic acid (C18:4) mead acid (C20:3), eicosadienoic acid (C20:3), eicosatrienoic acid (C20:3), dihomo-gamma-linolenic acid (C20:3), arachidonic acid (C20:4), and docosadienoic acid (C22:2).

In some embodiments, the adhesive matrix further comprises emulsifier or a penetration enhancer.

Emulsifier may include, without limitation, one or more of a glycerol ester (monoglycerides, diglycerides, triglycerides), polyoxyl stearate, a mixture of triceteareth-4 phosphate with ethylene glycol palmitostearate and with diethylene glycol palmitostearate, polyglyceryl-3 diisostearate, a mixture of PEG-6 stearate with ethylene glycol palmitostearate and with PEG-32 stearate, oleoylpolyoxyl-6 glycerides, lauroyl polyoxyl-6 glycerides, caprylocaproyl polyoxyl-8 glycerides, propylene glycol monocaprylate type I, propylene glycol monolaurate type II, propylene glycol monolaurate type I, propylene glycol monocaprylate type II, polyglyceryl-3 dioleate, a mixture of PEG-6 stearate with PEG-32 stearate, lecithin, cetyl alcohol, cholesterol, bentonite, veegum, magnesium hydroxide, dioctyl sodium sulfosuccinate, sodium lauryl sulfate, triethanolamine stearate, potassium laurate, polyoxyethylene fatty alcohol ethers, glyceryl monostearate, polyoxyethylenepoloxypropylene block copolymers (poloxamers), sorbitan monolaurate, lanolin alcohols and ethoxylated lanolin alcohols, sorbitan fatty acid esters, sucrose distearate, sodium alginate, alginic acid, hectorite, and aluminum silicate.

In some embodiments, the emulsifier is a glycerol ester (a product between glycerol and fatty acid). In some embodiments, the glycerol ester is selected from the group consisting of glycerol monooleate, glyceryl monotallate, and glyceryl trioleate.

Penetration enhancers may include one or more of ethanol, propanol, isopropanol, sulfoxides (e.g. decylmethyl or dimethyl sulfoxide), amides (e.g. dimethylformamide, azone, urea, dimethylacetamide), pyrrolidone derivatives (e.g. 1-methyl-4-carboxy-2-pyrrolidone, 1-methyl-2-pyrrolidone, 1-lauryl-4-methoxycarbonyl-2-pyrrolidone), terpenes (e.g. menthol, limonene, terpineol, pinene, carvol), ethyl acetate, methyl acetate, octisalate, pentadecalactone, n-dodecylcaprolactam (Azone), and acrylamide.

In some embodiments, the penetration enhancer is selected from dimethyl sulfoxide and n-dodecylcaprolactam (Azone).

In some embodiments, the molar amount of olanzapine corresponds to a therapeutically effective amount. In some embodiments, the therapeutically effective amount is between about 2-50 mg olanzapine.

In some embodiments, another matric-forming polymer can be included in the composition. Exemplary polymers include cellulose and its derivatives (such as but not limited to hydroxy methyl cellulose, Aquasolve™ hypermellose acetate succinate, hydroxypropyl methyl cellulose, hydroxypropyl cellulose, ethyl cellulose, hydroxyethyl cellulose, methyl cellulose, carboxymethyl cellulose, sodium carboxymethyl cellulose, microcrystalline cellulose blends, cellulose acetate phthalate, propylmethylcellulose phthalate. In some embodiments, the composition or adhesive matrix comprises ethyl cellulose.

In some embodiments, the adhesive matrix may further comprise a thickening agent such as silicon dioxide and polyvinyl pyrrolidone homopolymer and polyvinyl pyrrolidone copolymers such as but not limited to PVP, Kollidon 30, and poloxamer, a cross-linked polyvinylpyrrolidone, and vinylpyrrolidone-vinyl acetate copolymer.

Preservatives and stabilizers can be included in the composition, which may be selected from, without limitation, one or more of sodium metabisulfite, citric acid, ascorbic acid, vitamin E, BHA, Butylated Hydroxy Toluene (BHT), butylated hydroxyanisole, alpha tocopherol, acorbyl palmitate, propionic acid, sodium bisulfate, propyl gallate, monothioglycerol, ascorbic acid, sodium ascorbate, benzethoniumchloride, chlorhexidine, phenylethyl alcohol, chloroxylenol, cresol, hexetidine, phenoxyethanol, chlorobutanol, ascorbic acid, benzoic acid, sorbic acid, potassium sorbate, potassium metabisulfite, sodium metabisulfate, phenol, potassium benzoate, dehydroacetic acid, cetylpyridinium chloride, parabens, benzyl alcohol, benzalkonium chloride, and discoloring agents. In some embodiments, these agents are present in the range of 0.01% to about 30% w/w.

In some embodiments, the cross-linking agent, which may be selected from, without limitation, one or more of melamine formaldehyde (Aerotex® M3, Aerotex® 3730), is present in the range of 0.01% to about 30% w/w.

In some embodiments, the adhesive matrix comprises at least about 40 wt %, such as about 55 wt %, 65 wt %, 61 wt %, and 56 wt %, of the pressure sensitive adhesive.

In some embodiments, the adhesive matrix comprises between about 3-15 wt %, such as about 3 wt %, 3.5 wt %, 10.0 wt %, and 10.5 wt %, of the fatty ester.

In some embodiments, the adhesive matrix comprises between about 1-20 wt % such as 5-20 wt %, such as between about 6-15 wt %, about 7.4 wt %, 8 wt %, and 9 wt %, of the olanzapine.

In some embodiments, the adhesive matrix comprises between about 8-25 wt %, such as between about 8-20 wt %, about 10 wt %, 16 wt %, and 16.8 wt % and 9 wt %, of oleic acid.

In some embodiments, the amount of olanzapine is sufficient to deliver between 1-20 such as 1-12 mg olanzapine in 24 hours when the composition is applied to skin.

In some embodiments, the amount of olanzapine is sufficient to deliver olanzapine with an AUC thereof that is between 1% and 80%, 10% and 80%, 20% and 80%, 30% and 80%, or 40% and 80% of the exposure obtained from a standard of care treatment. The standard of care treatment comprises 2.5 mg, 4 mg, 5 mg, 6 mg, 8 mg, 10 mg, 15 mg, 20 mg, or 25 mg of olanzapine compound once daily or once every two days via oral administration.

Methods for preparing the compositions generally involve mixing the components (e.g, adhesives, olanzapine, oleic acid, and one of fatty alcohol, fatty acid, fatty ester, and optional stabilizer) together and let the resulting mixture dry.

IV. Transdermal Devices

In certain aspects, compositions disclosed herein are provided in transdermal devices (e.g., patches). In general, transdermal patches comprise a backing layer and at least one drug matrix layer. In some embodiments, transdermal patches further comprise one or more release liners, tie layers, rate-controlling membranes, and/or various combinations of the foregoing.

A patch may be formed, for example, without limitation, by solvent casting onto a backing layer or release liner, and sandwiching between both, as described herein. To avoid brittleness and impart flexibility to the adhesive matrix layer, one or more plasticizer can be added into the layer. The necessity and choice of plasticizer will depend on the particular adhesive and formulation. Suitable plasticizers are well known in the art. For example, without limitation, the one or more optional plasticizer may be selected from, without limitation, one or more of: glycols (in particular, without limitation, e.g. polyethylene glycol 400, polyethylene glycol 600, propylene glycol), higher alcohols (e.g. dodecanol), surfactants, sebacic acid esters (e.g. dibutyl sebacate, diethyl sebacate), citric acid esters (e.g. tributyl citrate, triethyl citrate), phthalic acid esters (e.g. diethyl phthalate, dibutyl phthalate), glycerol or glycerol esters (e.g. glycerine triacetate, glycerin), sugar alcohols (e.g. sorbitol, sucrose), tartaric acid esters (e.g. diethyl tartrate), oil (e.g. silicone oil, mineral oil), triacetin, oelic acid esters, adipate, and diisopropyl adipate. For inclusion into an adhesive patch formulation, and in particular an acrylic PSA patch formulation, preferred plasticizers include, without limitation, one or more of glycerol and glycerol esters. Further plasticizers may be found in "Handbook of Plasticizers" by George Wypych, 2004, Chem Tec Publishing), which is hereby incorporated by reference in its entirety. In certain embodiments, the plasticizers are present in the range of 0.01%-95% w/w.

Many suitable materials for the backing layer and release liner are known, and include polymer films, fabrics and non-woven materials, e.g. continuous films that prevent ingress of external moisture into the adhesive layer from activities such as showering or bathing. The backing and release liner should preferably be occlusive, or substantially occlusive. Such films include, without limitation, polypropylene, polyvinyl chloride, cellulose acetate, ethyl cellulose, polyurethane, polyethylene, and polyester. Optionally, the backing may be a layered composite that include a metal, such as, without limitation aluminum, e.g. polyethylene terephthalate-aluminium-polyethylene composites, or e.g. a polyester and an ethylene vinyl acetate copolymer heat seal layer (particularly as a backing), or e.g. a fluoropolymer coated polyester film (particularly as a release liner. Suitable backing layers include, without limitation, Scotchpak 1006, 1022, 1109, 9723, 9732, 9733 (3M company); suitable release liners include, without limitation, Scotchpak 1006, 9709, 9741, 9742, 9744, and 9755 (3M company). The thickness of the backing layer and of the release liner is generally more than 10 μm and less than 200 μm, typically about 20 μm to about 120 μm, e.g. about 40 μm to about 100 μm.

The coating formulation for the patch, may comprise volatile solvents which are removed from the patch matrix upon its drying; such volatile solvents include: methanol, ethanol, propanol, 1-propanol, 2-propanol, ethyl acetate, acetone, dichloromethane, chloroform, toluene, and IPA).

In some embodiments, the transdermal device for systemic delivery of olanzapine comprises a drug (matrix) comprising an acrylate polymer adhesive, a fatty ester, oleic acid, and olanzapine, and wherein the transdermal device when applied to skin delivers (i) an amount of olanzapine effective to alleviate nausea, vomiting, or both within a first period of between about 4-8 hours and (ii) an amount of olanzapine to alleviate nausea, vomiting or both for at least a sustained period of between about 1-7 days.

In some embodiments, the transdermal device when applied to (human cadaver) skin in vitro has an average flux during the sustained period of at least about 4 µg/cm²·hr.

In some embodiments, the sustained period is between about 2-7 days or between 2-5 days.

In some embodiments, the amount of olanzapine delivered in the first period and the sustained period is at least about 3 mg per day.

In some embodiments, wherein the amount of olanzapine delivered in the first period and the sustained period is between about 3-6 mg per day.

In some embodiments, the drug matrix comprises between about 1-20 wt % such as 5-20 wt % olanzapine.

In some embodiments, the transdermal device for delivery of olanzapine, comprising: a drug matrix comprising an acrylate polymer adhesive, a fatty ester, oleic acid, and olanzapine, and wherein the transdermal device when applied to skin in vitro has a flux profile where (i) a maximum flux rate is achieved within about 36-54 hours, (ii) between about 65-80% of the maximum flux rate is achieved within about 18-36 hours, and (iii) an average flux rate of at least about 3 µg/cm²·hr for a period of between about 1-7 days is achieved.

In some embodiments, the average flux rate is for a period of between about 1-3 or 1-5 days.

In some embodiments, wherein the flux profile provides over the period an amount of olanzapine effective to alleviate nausea, vomiting, or both.

Usage of the described transdermal and topical systems described here will have dosages that vary depending on the mode of administration, the particular condition to be treated and the effect desired. Dosage may be transdermal application once daily for 1 day, 2 days, 3, day, 4 days, 5, days, 6 days, 7 days, 8 days, 9 days, 10 days, 11 days, 12 days, 13 days, or 14 days, or longer. Alternatively, application may be several times a day for 1 day, 2 days, 3, day, 4 days, 5, days, 6 days, 7 days, 8 days, 9 days, 10 days, 11 days, 12 days, 13 days, or 14 days, or longer. Alternatively transdermal application may be once every day, every 2 days, every 3 days every 4 days, every 5 days, every 6 days, every 7 days, every 8 days, every 9 days, every 10 days, every 11 days, every 12 days, every 13 days, or every 14 days.

In some embodiments, the transdermal or topical formulations provide for a predetermined rate of delivery of the active components of the transdermal patch over a predetermined time period. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is a constant rate.

In yet further embodiments, the transdermal or topical formulations described herein provide a steady absorption rate of the active components of the transdermal patches by the patient over a predetermined time. In some embodiments, the predetermined time period is 24 hours, 48 hours, 72 hours, 96 hours, 120 hours, 144 hours, 7 days, 8 to 13 days, two weeks, or 15 days. In some further embodiments, the predetermined rate is a constant rate.

In yet further embodiments, the transdermal or topical formulations described herein provide a range of predetermined blood serum levels of the active components of the transdermal patches in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations described herein provide a plasma concentration of the active components of the transdermal patches in a therapeutic range in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In yet further embodiments, the transdermal or topical formulations described herein allow for reduced variability in dosage of the active components in a patient over a predetermined time. In some embodiments, the predetermined time period is 24 hours, 48 hours, 72 hours, 96 hours, 120 hours, 144 hours, 7 days, 8 to 13 days, two weeks, or 15 days.

In some embodiments, the transdermal or topical formulation provided herein may be administered in dosage regimens such as once in a day, once in two days, once in three days, once in four days, once in five days, once in six days, once in a week, once in 8 to about 13 days, once in two weeks, once in 15 days to about 30 days.

In yet further embodiments, a pharmacokinetic assessment is performed on a blood sample of a subject who has been treated using the transdermal delivery systems described herein. The transdermal formulations described herein are adjusted in response to the pharmacokinetic assessment. For example, the dosage may be adjusted such that a smaller patch, larger patch, or multiple transdermal patches are applied to the subject, or a patch having a more or less of a dose of active ingredients may be applied. In some embodiments, the formulation will be available in various dosage strengths and patch sizes in order to achieve optimum therapeutic outcome based on the subject's requirements.

Example 1 describes preparation of olanzapine transdermal patches labeled as OLA 1, OLA 2, OLA 3, OLA 4, OLA 5, OLA 6, and OLA 7.

In the permeation study as described in Example 2, using OLA 1 as an example, the flux increased rapidly reaching 72% of maximum within the first 24 hours and maximum at about 48 hours. After this, the transdermal flux gradually decreased at a steady rate to about 61% of maximum at 168 hours. The average flux from 24 to 168 hours for 11 donors (50 total replicates) was 4±1.3 ug/hr/cm². See FIG. 7.

Example 3 compares the cold flow property of two compositions. The results indicated that composition with an additional polymer such as ethyl cellulose has reduced cold flow.

V. Antiemetic Effect of Olanzapine

Olanzapine for prevention of nausea and vomiting has been tested at doses of 10 mg and a few studies at 5 mg a day, but without a pharmacodynamic evaluation. No studies have evaluated the minimum effective dose in nausea and vomiting. One side effect of olanzapine is fatigue/sedation, which is problematic in certain types of cancer therapy and olanzapine causes sedation.

Transdermal delivery of drugs can be likened to a continuous intravenous infusion, in that drug is absorbed directly into the blood at a steady rate during the entire application of the patch. One advantage to transdermal patch delivery is that the high blood levels (maximum) and low blood levels (minimum) are avoided. In the case of most drugs, the maximum concentration (Cmax) is associated with toxicity of the drug and the minimum concentration (Cmin) is usually below the required therapeutic blood level. Usually, the target for the patch is the blood level, which provides the same area under the time concentration curve (AUCO-∞) over the dosing interval. AUCO-∞ is a measure of total drug exposure.

As a result, the blood level target that emulates an oral administration requires the determination of the blood ranges at the maximum and minimum levels both on the first dose as well as at steady state. This target modeling can be estimated in silico using traditional pharmacokinetic models based on the in vitro flux of the drug in cadaver skin testing systems (Franz Cell).

FIG. 1 below shows an in silico modeling of oral olanzapine over a 7-day dosing interval which achieves steady state at doses of 10 mg, 5 mg, and 2.5 mg a day, respectively from published data (Polasek T et al. *Br J Clin Pharmacol* (2018) 84 462-476). The black lines at each dosing level represent the planned patch blood level targets to emulate each specific oral dose. Despite the ability to model these data, human in vivo studies are required to validate the data used in the model.

Example 1 describe a phase 1 study of antiemetic effect of four doses of oral olanzapine. The primary objective of the study was to assess the antiemetic effectiveness, following an apomorphine challenge on day 8, of 4 different doses of olanzapine or a placebo administered for 8 days and identify the target blood levels needed for the proposed optimal dose.

This study indicated the optimal dose for nausea and vomiting identified was 6 mg a day while the minimum effective dose for nausea was 4 mg a day based on the planned statistical integration of the nausea scores and the incidence of retching and vomiting.

Figure 2:
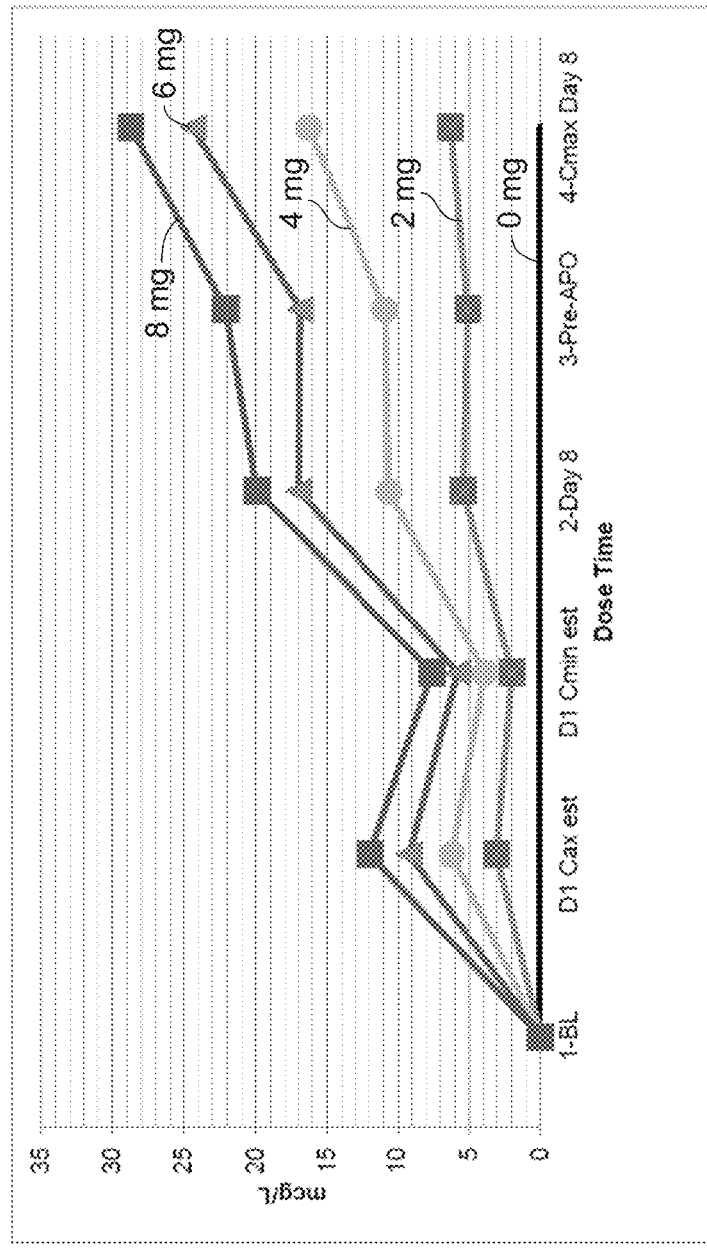
FIG. 2 shows olanzapine plasma levels by oral dose obtained in a phase 1 study.

FIG. 2 provides the blood levels at Cmax and Cmin for olanzapine by dose group. The target blood levels at steady state for the transdermal patch ranged (Cmin to Cmax) from 11-16 mcg/L for the 4 mg dose and 17-24 mcg/L for the 6 mg dose, while the day 1 blood levels (which are effective in CINV) ranged from 4-6 mcg/L for the 4 mg dose and 6-9 mcg/L for the 6 mg dose. The targets are selected by calculating the mid-point of the blood level range at both day 1 and steady state. To achieve the 6 mg a day optimal dose equivalent, a target steady state blood level is 20 mcg/L with a 1-day level of 8 mcg/L. For the 4 mg a day minimum dose equivalent, a target steady state blood level is 13 mcg/L with a 1-day level of 5 mcg/L.

Figure 3:
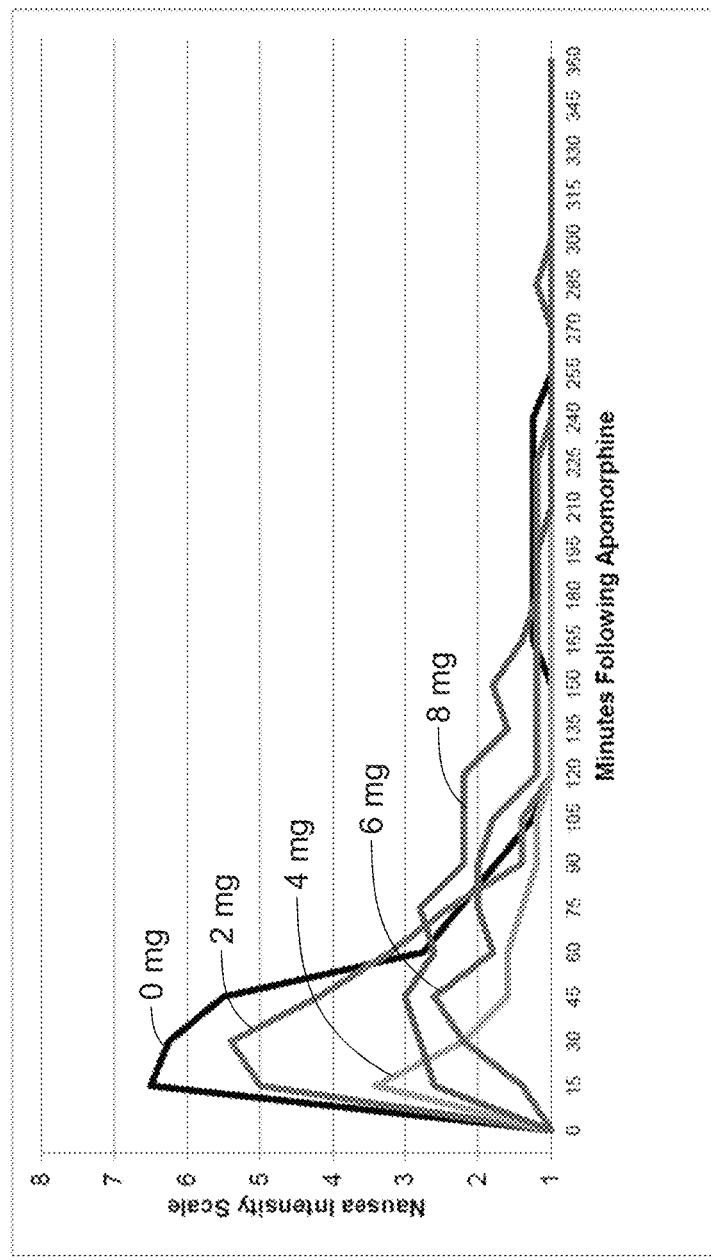
FIG. 3 shows nausea severity following apomorphine challenge.

FIG. 3 shows nausea severity following apomorphine challenge. Nausea scores measured every 15 minutes over 6 hours where 1=no nausea and 10=severe nausea. The development of nausea following an apomorphine challenge was observed within 15 minutes with the maximum intensity between 15-45 minutes. In nearly all subjects, nausea was not present after 120 minutes (except for the 8 mg dose level) following the apomorphine challenge. The maximum intensity of nausea was no different between the 4 mg, 6 mg, and 8 mg-dose, however, nausea intensity observed over the 120 minute interval with the 8 mg dose was not different from the placebo control.

Figure 4:
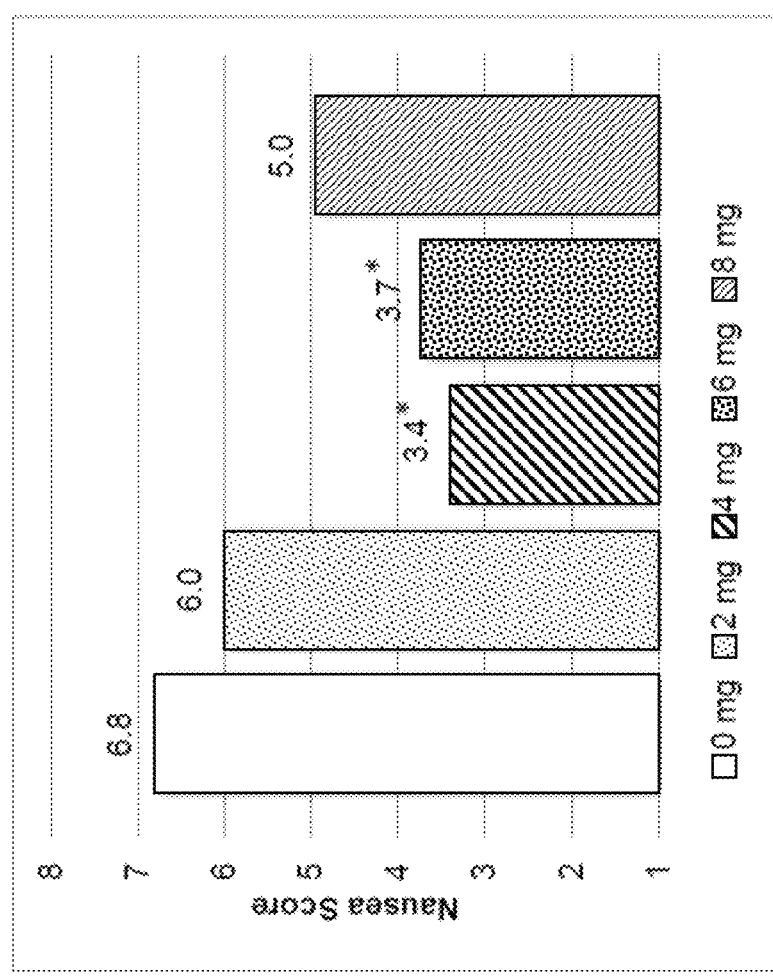
FIG. 4 shows nausea score following apomorphine challenge.

FIG. 4 shows nausea score following apomorphine challenge. Nausea severity scores during the 0-120 min following an apomorphine challenge where 1=no nausea and 10=severe nausea. The 4 mg and 6 mg olanzapine steady state doses were significantly different than placebo ($p<0.05$) but not significantly different from each other. The 2 mg and 8 mg olanzapine doses were not significantly different than placebo.

Figure 5:
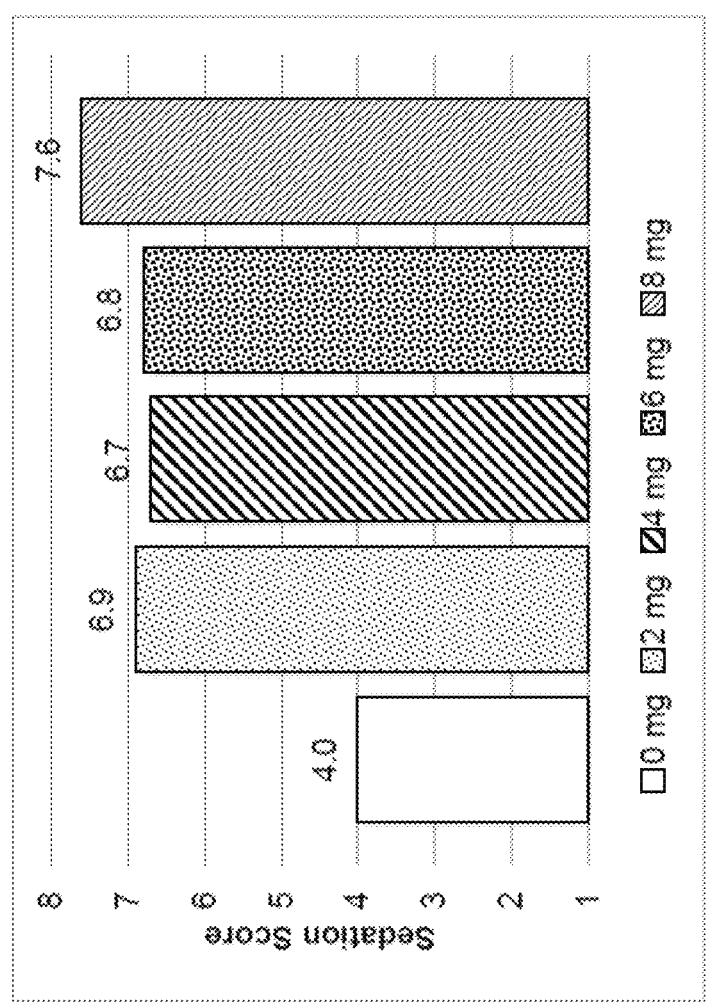
FIG. 5 shows sedation score following day of oral olanzapine by dose.

FIG. 5 shows sedation score following 1 day of oral olanzapine by dose. Sedation severity scores on day 1 of olanzapine treatment where 1=no sedation and 10=severe sedation. All of the olanzapine doses were significantly different (higher sedation) than placebo. The incidence of sedation on day 1 was significantly greater in all doses of olanzapine than placebo. These data demonstrate that the sedation observed in the first day of dosing with olanzapine is NOT dose dependent and occurs at a similar intensity across the tested doses. This is the first ever report of the lack of dose relationship for sedation with olanzapine over the doses tested. The sedation appears to be only different from placebo on the first day of dosing and is not of significant intensity after day 1.

Figure 6:
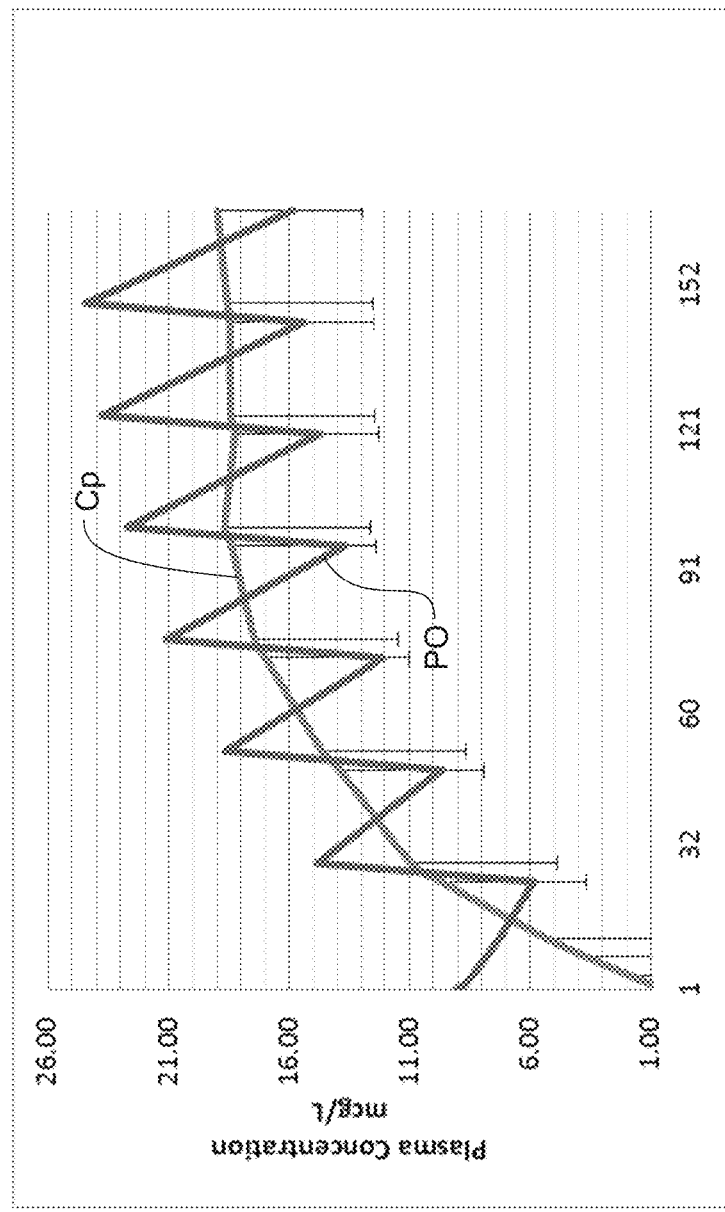
FIG. 6 modeled blood targets of olanzapine patch to emulate a 6 mg a day dose with error bar to the 4 mg dose.

FIG. 6 shows a modeled blood targets of olanzapine patch to emulate a 6 mg a day dos with error bar to the 4 mg. A revised model was generated based on the observed in vivo blood concentrations at 6 mg a day from this study. In addition the lower level for an acceptable blood level associated with variability of the flux is represented by the lower error bar. The estimated patch size for this deliver is 65 $cm^2$.

VI. Examples

The following examples are illustrative in nature and are in no way intended to be limiting.

Example 1

Antiemetic Effect of Different Oral Doses of Olanzapine

This study was an exploratory phase 1 design to determine the minimal effective dose of olanzapine as represented by the plasma concentration. Twenty-four healthy female volunteers were enrolled. Four active-treatment groups and a cohort of placebo-treated subjects were evaluated. The oral dose assignments in each cohort were: (1) olanzapine 2.0 mg a day (n=5) or placebo (n=1), (2) olanzapine 4.0 mg a day (n=5) or placebo (n=1), (3) olanzapine 6.0 mg a day (n=5) or placebo (n=1), and (4) olanzapine 8.0 mg a day (n=5) or placebo (n=1).

Subjects were administered study drug once daily for 8 days. During this period, subjects maintained a study diary of their side effects. The subject diary was used to collect on a daily basis any adverse events including an assessment of the presence and/or intensity of sedation on a numeric scale where 1=no sedation and 10=excessive sedation.

On the 8th day, subjects were administered apomorphine at a dose of 0.05 mg/kg and assessed over 6 hours. During this period, subjects were asked to record episodes of nausea on a numeric scale every 15 minutes for the duration of assessment. The intensity of nausea was captured using a 1-10 rating scale where 1=no nausea and 10=severe nausea. Emesis intensity was also captured where 1=no emesis and 10=severe emesis. Episodes of retching or emesis were collected and measured for the absolute number of retches or vomits during the collection period and documented for the time of the specific event following the administration of the apomorphine.

Blood samples were obtained for olanzapine measurement prior to study drug administration on day 1, on day 8 before the last dose of olanzapine was administered, just prior to the administration of the apomorphine challenge, and just prior to discharge from the CRU after the 6-hour observation. To aid in understanding the change in blood levels from the first dose to last dose of olanzapine, published data was used to project the day 1 Cmax and Cmin (trough) (Polasek T et al. *Br J Clin Pharmacol* (2018) 84 462-476).

The frequency of sedation was categorized over the 8-day olanzapine-dosing interval as a percent of subjects who experience sedation. The intensity of sedation was categorized using the area under the curve (AUC) of the intensity scale over the 8 day dosing period. The frequency of nausea was categorized as a percent of subjects who experienced no nausea. The intensity of nausea was calculated using the AUC of the intensity scale over the 6 hour observation period following apomorphine. The frequency of emesis was categorized as a percent of subjects who experienced no emesis. The intensity of emesis was categorized using the AUC of the intensity scale over the 6 hour observation period. The frequency of retching was categorized as a percent of subjects who experienced no retching. The intensity of retching was categorized using the AUC of the intensity scale over the 6 hour observation period. The minimum effective dose was determined with a predetermined method. The steady state trough and pre-apomorphine plasma olanzapine concentrations was integrated by dose group. The data was ranged to provide a target blood level for each equivalent oral dose.

The table below lists the incidence of nausea, retching, vomiting, and sedation by dose level.

|  | 0 mg | 2 mg | 4 mg | 6 mg | 8 mg |
|---|---|---|---|---|---|
| Nausea Score | 6.9 | 6** | 3.4 # | 3.7 # | 5** |
| 1-120 min. | Moderate | Moderate | Mild | Mild | Mild |
| Retching | 50% | 40% | 0% | 0% | 20% |
| Vomiting | 50% | 40% | 20% | 0% | 20% |

**vs 0 mg p = NS
: lower vs 0 mg p < 0.05

The optimal dose for nausea and vomiting identified was 6 mg a day while the minimum effective dose for nausea was 4 mg a day based on the planned statistical integration of the nausea scores and the incidence of retching and vomiting.

FIG. 2 shows the blood levels of olanzapine by oral dose. From FIG. 2, one can identify the targeted steady state blood level (20 mcg/L and 13 mcg/L for 6 mg/day and 4 mg/day, respectively) and 1-day level (8 mcg/L and 5 mcg/L for 6 mg/day and 4 mg/day, respectively). FIG. 3-5 show nausea severity following apomorphine challenge, nausea score following apomorphine challenge, and sedation score following 1 dat of oral olanzapine dose, respectively.

FIG. 6 shows a modeled blood targets of Olanzapine Patch to emulate an oral 6 mg/day dose with error bar to the 4 mg dose.

Example 2

Preparing an Olanzapine Transdermal Patch

The compositions for transdermal delivery were prepared by mixing the ingredients in the table below in a solvent such as ethyl acetate.

| Ingredient | OLA 1 | OLA 2 | OLA 3 | OLA 4 | OLA 5 | OLA 6 | OLA 7 |
|---|---|---|---|---|---|---|---|
| Olanzapine | 9.0% | 7.4% | 8.0% | 8.0% | 8.0% | 8.0% | 8.0% |
| Oleic acid | 10.0% | 16.8% | 16.0% | 16.0% | 16.0% | 16.0% | 16.0% |
| DMSO | 16.0% | — | — | — | — | — | |
| Isopropyl Palmitate | 3.5% | 10.5% | 10.0% | 10.0% | 10.0% | 10.0% | 10.0% |
| Myristyl Alcohol | 3.0% | — | — | — | — | — | |
| GMO (Croda) | 3.5% | — | — | — | — | — | |
| Kollidon CL-M (BASF) | — | — | 5.0% | — | — | — | |
| Kollidon VA 64 (BASF) | — | — | — | 5.0% | — | — | |
| Aerosil 200 Pharma (SiO2) | — | — | — | — | 5.0% | — | |
| Aqualon EC-N50 Pharma (ethyl cellulose) | — | — | — | — | — | 5.0% | 10.0% |
| Butylated Hydroxy Toluene (BHT) | — | 0.5% | 0.5% | 0.5% | 0.5% | 0.5% | 0.5% |
| Duro-Tak 87-9301 | 55.0% | 64.7% | 60.5% | 60.5% | 60.5% | 60.5% | 55.50% |

The following steps are provided using composition OLA 1 as an example for preparing a transdermal patch. The above ingredients are blended by stirring for 18 hours and then, using a commercial benchtop spreader, the matrix is evenly spread onto an 8×14 inch sheet of release liner (such as 3M 9744) to a thickness of 0.5 mm. The sheet is then place in an oven at 100 F for one hour to evaporate off the ethyl acetate adhesive solvent. An opaque backing membrane (such as 3M 9730 NR film) with low permeability to oxygen to inhibit photo and oxidative degradation, is then carefully applied by hand to avoid formation of bubbles and voids. A circular die (1.5 inches diameter) is used to cut patches (7 sqcm) for subsequent studies. The average weight of a sample (n=52) of patches is 213 mg. Since the average weight of a sample of backing membranes and release liners is 124 mg, the calculated weight of the adhesive matrix is 89 mg. Thus, after drying, the drug adhesive matrix has a surface density of 13 mg/sqcm, containing 9% or 1.2 mg/sqcm of olanzapine.

Example 3

In Vitro Transdermal Flux Measurement

The general procedure for flux measurement of the transdermal patch is as follows. The release liner is peeled off the patch and the adhesive surface is applied to a piece of human cadaver skin. The skin, stored as a sheet frozen on dry ice, is thawed at room temperature water, and visually inspected for defects before the patch is applied. Transdermal flux is measured in standard Franz diffusion cells composed of a cylindrical donor compartment and a separate water jacketed cylindrical receptor compartment. The skin is clamped between the two compartments with the subdermal side facing the receptor compartment. The receptor compartment is filled with receptor medium, held at constant temperature, and constantly stirred to collect the olanzapine as it diffuses through the skin and into the receptor compartment. The receptor compartment is emptied at 24 hr intervals for assay of olanzapine and replaced with fresh receptor solution. The concentration of olanzapine in the receptor compartment never exceeds 10% of its solubility so that sink conditions are maintained. The table below lists the flux assay conditions.

| In Vitro Flux assay Conditions | |
|---|---|
| Receiving Media | PBS, 0.01% Na azide, pH 6.5 |
| Receiving media Volume | 13 mL |
| Volume sampled | 13 mL |
| Sampling interval | 24 hours |
| Franz cell surface area for diffusion | 1.76 cm$^2$ |

Figure 7:
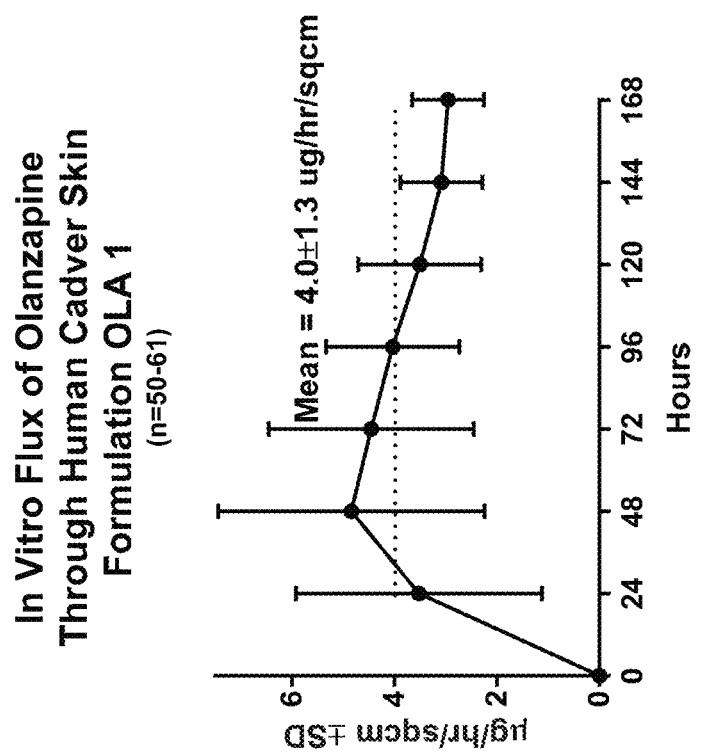
FIG. 7 shows the in vitro flux of olanzapine through human cadaver skin versus time.

Flux is measured for a period of 7 days (or 168 hours), except for 2 experiments only for 6 days. FIG. 7 is the in vitro flux chart for composition OLA 1. Compositions OLA 2-6 were also tested in the flux assay by following the procedure described above. The table below lists the mean flux rate for each of the formulations.

| | OLA 1 | OLA 2 | OLA 3 | OLA 4 | OLA 5 | OLA 6 |
|---|---|---|---|---|---|---|
| Flux 24 Hr (n = 3) | 2.4 (57%) | 1.3 (25%) | 2.0 (38%) | 1.9 (46%) | 2.1 (62%) | 3.0 (50%) |
| Flux 24-144 Hrs (n = 3) | 4.4 (7%) | 3.8 (9%) | 4.1 (14%) | 3.9 (11%) | 3.5 (20%) | 4.2 (6%) |

(%) refers to relative standard deviation.

Example 4

Cold Flow Study

Patches were cut with a 7 cm² die and subjected to compression with a 1 kg weight as follows: (1) the release liner was removed from the patch, and then the patch was carefully applied to the fluoropolymer side of a fresh 3.5×3.5 square of release liner, (2) another 3.5×3.5 square of release liner, fluoropolymer side down, was placed on top of the patch so that the patch was now sandwiched between two layers of release liner, (3) a 1 kg weight was carefully applied on top of the patch in order to avoid any lateral movement and left in place for 3 days, (4) at the end of 3 days, the weight was carefully removed and the % increase in surface area was measured. The results are below.

| | OLA 1 | OLA 2 | OLA 3 | OLA 4 | OLA 5 | OLA 6 |
|---|---|---|---|---|---|---|
| Cold Flow (% Relative Standard Deviation) | 20.41 (44%) | 13.09 (11%) | 14.08 (19%) | 8.62 (20%) | 4.25 (15%) | 2.63 (21%) |

Example 5

Comparative Bioavailability Study of Olanzapine Transdermal Patch with Oral Olanzapine A comparative bioavailability study was conducted to identify the optimal formulation for the clinical studies and assess the bioavailability of a transdermal patch as described herein compared to oral olanzapine at the primary published dose of 10 mg/day in Chemotherapy Induced Nausea and Vomiting.

This study is a cohort-assigned, open label study with 3 cohorts of approximately 12 subjects in each cohort. Subjects were cohort-assigned 1:1:1 to either OLA 1-1×35 cm² patch (Group 2), or OLA 1-2×35 cm² patches (Group 3) or 10 mg oral Zyprexa® (Group 1) for seven consecutive days. Treatment for each of the OLA 1 cohorts was administered as a patch(es) applied to the deltoid region of the body. The 10 mg oral Zyprexa® treatment was administered with 240 mL of water daily at the same time each morning. A total of approximately 36 healthy volunteers, ages 18 to 55 years inclusive were enrolled in this study. A diary was dispensed to each subject and daily self-evaluations of the level of sedation and hunger on a numeric scale was assessed on an ordinal score of 0-10 twice a day. The daily self-evaluations of the level of sedation and hunger continued to the morning of day 13.

On Day 1 OLA 1 patches were placed on the cohort-assigned subjects and remained on them through Day 8 or cohort-assigned subjects were administered 10 mg oral Zyprexa® QD with 240 mL of water for 7 days (not given on day 8). Water consumption will be restricted for 1 hour after dosing.

Blood samples for pharmacokinetic (PK) analysis were obtained at the following times: pre-dose (within 30 minutes prior to dosing) and 1, 2, 4, 8, 12, 24, 28, 48, 52, 72, 76, 96, 100, 120, 124, 144, 148, and 168 hours (+/−15 minutes); then for time points 192, 216, 240, 264, and 288 hours (+/−2 hours) after initial dose administration. For patch cohort, blood sample was taken each am at the same time, 4 hours after morning trough sample. For oral Zyprexa® cohort, PK sample was taken (trough), and 4 hours post-dose.

Figure 8:
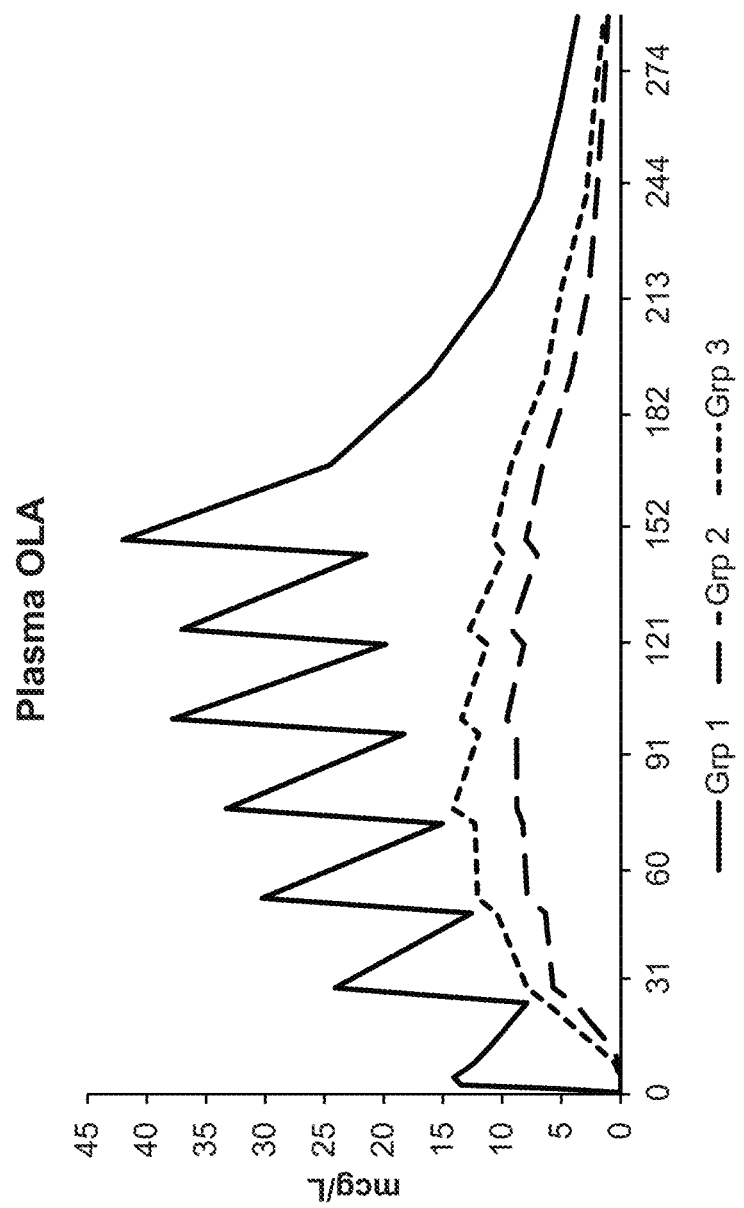
FIG. 8 compares the plasma level of olanzapine for three dose groups: Group 1-10 mg olanzapine oral once daily, Group 2-1×35 cm$^2$ patch containing olanzapine, and Group 3—2×35 cm$^2$ patches containing olanzapine.

The median plasma level of olanzapine from each cohort group as a function of time in hours is shown in FIG. 8.

The table below summarizes pharmacokinetic information for the three cohort groups. The total dose for Group 2 and 3 was apparent dose absorbed during the 7-day study. The apparent dose was obtained after a mass balance study/calculation. In the mass balance study, post study testing for the residual olanzapine that remained in the patch dosage form after removal was assayed using a validated method. The difference between the drug load (47.25 mg/patch) and the residual is the apparent dose of the table below:

| | Total Dose Over 7 days (mcg) | AUC (mcg/L/h) | Mean Cmax (mcg/L) during 7 days | Average Daily Dose (mcg) over 7 days | % BA by AUC to 10 mg Oral |
|---|---|---|---|---|---|
| Group 1 | 70,000 | 5,287 | 41.6 | 10,000 | 100% |
| Group 2 | 22,770 | 1,496 | 9.3 | 3,252 | 28.3% |
| Group 3 | 34,850 | 2,117 | 13.2 | 4,980 | 40.0% |

Figure 9:
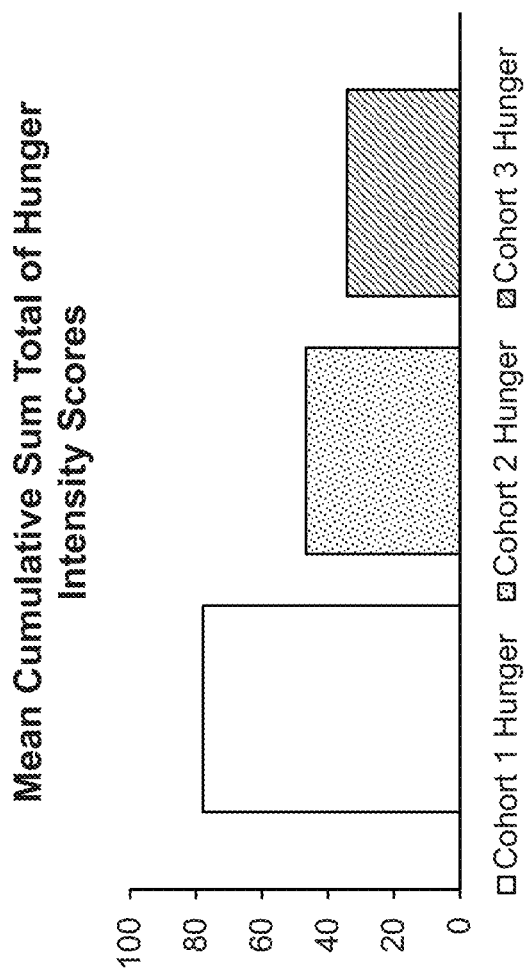
FIG. 9 shows mean cumulative sum total of hunger intensity scores over a study for two cohort groups administered with one or two olanzapine-containing transdermal patches and one cohort group administered with olanzapine orally.
Figure 10:
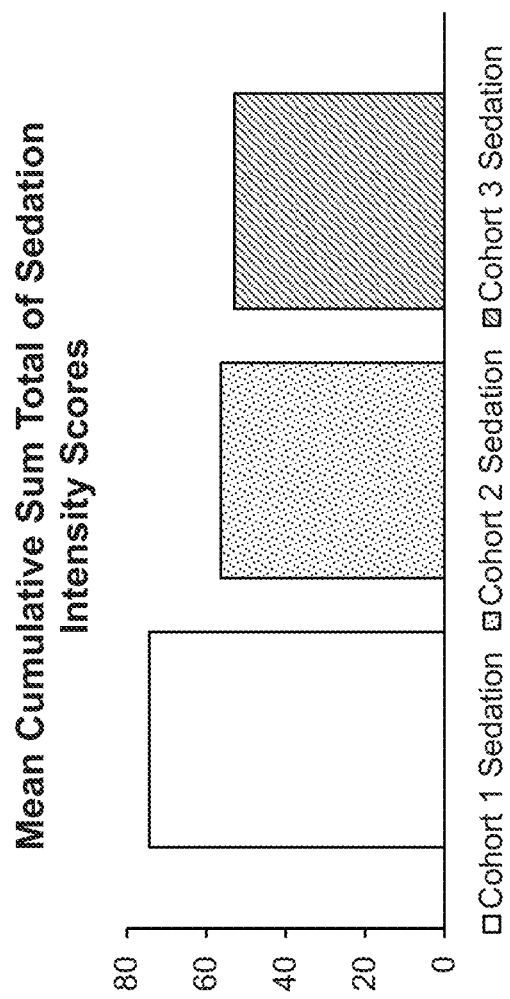
FIG. 10 shows mean cumulative sum total of sedation intensity scores over a study for two cohort groups administered with one or two olanzapine-containing transdermal patch and one cohort group administered with olanzapine orally.

FIG. 9 and FIG. 10 list the mean cumulative sum total of intensity scores for hunger and sedation, respectively, by cohort groups over the study, respectively.

EQUIVALENTS

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

All patents, patent applications, patent publications, and other publications mentioned herein are hereby incorporated by reference in their entirety. Where a patent, application, or publication contains express definitions, those definitions should be understood to apply to the incorporated patent, application or publication in which they are found and not to the present application unless otherwise indicated.

It is claimed:

1. A method for preventing or reducing the frequency and/or intensity of vomiting (emesis) and/or nausea associated with chemotherapy, comprising: administering olanzapine transdermally in an amount greater than about 2 mg and less than about 8 mg per day in combination with a fatty alcohol, a fatty ester, or a combination thereof in a drug-in-adhesive formulation, wherein an average flux rate of olanzapine of at least 3 µg/cm²/hr is achieved continuously throughout a period of at least 3 days after administration.

2. The method of claim 1, wherein said transdermal administration provides a plasma concentration of olanzapine i) 24 hours after administration of at least about 7 µg/L, ii) 48 hours after administration of greater than about 11 µg/L, and iii) 60 hours after administration of greater than about 15 µg/L.

3. The method of claim 1, wherein said transdermal administration provides a plasma concentration of olanzapine 24 hours after administration of at least about 6 µg/L and achieves a steady state plasma concentration of olanzapine of about 16-24 µg/L for a period beginning at a time 24 hours after administration and continuing for at least about 2 days.

4. The method of claim 1, wherein said transdermal administration provides a plasma concentration of olanzapine 24 hours after administration of at least about 8 µg/L and achieves a steady state plasma concentration of olanzapine of about 18-22 µg/L for a period beginning at a time 24 hours after administration and continuing for at least about 2 days.

5. The method of claim 1 wherein sedation resulting from said administering is essentially unchanged relative to an olanzapine oral dose of about 2 mg.

6. The method of claim 1, wherein the chemotherapy is emetogenic cancer chemotherapy.

7. The method of claim 1, wherein transdermally administering comprises applying to skin of a human subject a composition, the composition comprising: (i) at least about 40 wt % of a pressure-sensitive adhesive; (ii) between about 3-15 wt % of the fatty ester, the fatty alcohol, or a combination thereof; and (iii) between about 1-20 wt % olanzapine.

8. The method of claim 1 comprising: transdermally administering olanzapine to a subject in need thereof in a dose ranging from 2.0 mg to 6.0 mg daily.

9. The method of claim 1 comprising: transdermally administering olanzapine to a subject in need thereof, wherein the method achieves an AUC of olanzapine ranging from 1000 to 2500 µg/L/h.

10. The method of claim 1 comprising: transdermally administering olanzapine to a subject in need thereof, wherein the method achieves a mean Cmax ranging from 5 to 20 µg/L.

11. The method of claim 1 comprising: transdermally administering olanzapine to a subject in need thereof, wherein the method achieves an AUC of olanzapine of between 20% and 80% of the AUC obtained from a standard of care treatment.

* * * * *